US009907890B2

(12) United States Patent
Muller

(10) Patent No.: US 9,907,890 B2
(45) Date of Patent: Mar. 6, 2018

(54) CATHETER PUMP WITH POSITIONING BRACE

(71) Applicant: TC1 LLC, Pleasanton, CA (US)

(72) Inventor: Paul F. Muller, San Carlos, CA (US)

(73) Assignee: TC1 LLC, Pleasanton, CA (US)

( * ) Notice: Subject to any disclaimer, the term of this patent is extended or adjusted under 35 U.S.C. 154(b) by 0 days.

(21) Appl. No.: 15/130,170

(22) Filed: Apr. 15, 2016

(65) Prior Publication Data

US 2016/0303299 A1 Oct. 20, 2016

Related U.S. Application Data

(60) Provisional application No. 62/148,420, filed on Apr. 16, 2015.

(51) Int. Cl.
*A61M 1/00* (2006.01)
*A61M 1/10* (2006.01)
*A61M 1/12* (2006.01)

(52) U.S. Cl.
CPC .......... *A61M 1/1012* (2014.02); *A61M 1/102* (2014.02); *A61M 1/1008* (2014.02); *A61M 1/1013* (2014.02); *A61M 1/1017* (2014.02); *A61M 1/1031* (2014.02); *A61M 1/101* (2013.01); *A61M 1/1024* (2014.02); *A61M 1/1034* (2014.02); *A61M 1/122* (2014.02); *A61M 1/125* (2014.02)

(58) Field of Classification Search
CPC ............................ A61M 1/1012; A61M 1/125
USPC ........................................................ 600/16
See application file for complete search history.

(56) References Cited

U.S. PATENT DOCUMENTS 1,902,418 A 3/1933 Pilgrim
2,356,659 A 10/1942 Aguiar
(Continued)

FOREIGN PATENT DOCUMENTS

CA 2701810 4/2009
EP 0 533 432 9/1992
(Continued)

OTHER PUBLICATIONS

Abiomed, "Impella 5.0 with the Impella Console, Circulatory Support System, Instructions for Use & Clinical Reference Manual," Jun. 2010, in 122 pages.
(Continued)

*Primary Examiner* — Nadia A Mahmood
(74) *Attorney, Agent, or Firm* — Armstrong Teasdale LLP

(57) ABSTRACT

A catheter pump assembly is provided that includes an elongate body assembly, a shaft, and an impeller. The assembly has a proximal end, a distal end and at least one lumen extending therebetween. The shaft is disposed at least partially within the elongate body, e.g., in the at least one lumen, and journaled for rotation. The impeller is coupled with a distal portion of the shaft. The impeller is configured to be rotated to induce flow of blood when the impeller is placed in fluid communication with a source of blood. An inflatable balloon brace is disposed on an outer surface of the catheter pump. The inflatable balloon brace is spaced proximally of the impeller and has a low profile configuration for delivery through the vasculature and an expanded configuration for disposing (e.g., position and/or orienting) the impeller within the source of blood.

21 Claims, 23 Drawing Sheets

(56) References Cited

U.S. PATENT DOCUMENTS

| | | |
|---|---|---|
| 2,649,052 A | 8/1953 | Weyer |
| 2,664,050 A | 12/1953 | Abresch |
| 2,684,035 A | 7/1954 | Kemp |
| 2,789,511 A | 4/1957 | Warren |
| 2,896,926 A | 7/1959 | Chapman |
| 2,935,068 A | 5/1960 | Donaldson |
| 3,080,824 A | 3/1963 | Boyd et al. |
| 3,455,540 A | 7/1969 | Marcmann |
| 3,510,229 A | 5/1970 | Smith |
| 3,812,812 A | 5/1974 | Hurwitz |
| 3,860,968 A | 1/1975 | Shapiro |
| 3,904,901 A | 9/1975 | Renard et al. |
| 3,995,617 A | 12/1976 | Watkins et al. |
| 4,115,040 A | 9/1978 | Knorr |
| 4,129,129 A | 12/1978 | Amrine |
| 4,135,253 A | 1/1979 | Reich et al. |
| 4,143,425 A | 3/1979 | Runge |
| 4,149,535 A | 4/1979 | Volder |
| 4,304,524 A | 12/1981 | Coxon et al. |
| 4,382,199 A | 5/1983 | Isaacson |
| 4,392,836 A | 7/1983 | Sugawara |
| 4,458,366 A | 7/1984 | MacGregor |
| 4,540,402 A | 9/1985 | Aigner |
| 4,560,375 A | 12/1985 | Schulte et al. |
| 4,589,822 A | 5/1986 | Clausen et al. |
| 4,625,712 A | 12/1986 | Wampler |
| 4,655,745 A | 4/1987 | Corbett |
| 4,686,982 A | 8/1987 | Nash |
| 4,704,121 A | 11/1987 | Moise |
| 4,728,319 A | 3/1988 | Masch |
| 4,753,221 A | 6/1988 | Kensey et al. |
| 4,769,006 A | 9/1988 | Papantonakos |
| 4,817,586 A | 4/1989 | Wampler |
| 4,846,152 A | 7/1989 | Wampler et al. |
| 4,895,557 A | 1/1990 | Moise et al. |
| 4,900,227 A | 2/1990 | Trouplin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,944,722 A | 7/1990 | Carriker et al. |
| 4,955,856 A | 9/1990 | Phillips |
| 4,957,504 A | 9/1990 | Chardack |
| 4,964,864 A | 10/1990 | Summers et al. |
| 4,969,865 A | 11/1990 | Hwang et al. |
| 4,976,270 A | 12/1990 | Parl et al. |
| 4,985,014 A | 1/1991 | Orejola |
| 4,994,017 A | 2/1991 | Yozu |
| 4,995,857 A | 2/1991 | Arnold |
| 5,000,177 A | 3/1991 | Hoffman et al. |
| 5,021,048 A | 6/1991 | Buckholtz |
| 5,045,072 A | 9/1991 | Castillo et al. |
| 5,049,134 A | 9/1991 | Golding et al. |
| 5,061,256 A | 10/1991 | Wampler |
| 5,089,016 A | 2/1992 | Millner et al. |
| 5,092,844 A | 3/1992 | Schwartz et al. |
| 5,098,256 A | 3/1992 | Smith |
| 5,106,368 A | 4/1992 | Uldall et al. |
| 5,112,200 A | 5/1992 | Isaacson et al. |
| 5,112,292 A | 5/1992 | Hwang et al. |
| 5,112,349 A | 5/1992 | Summers et al. |
| 5,129,883 A | 7/1992 | Black |
| 5,142,155 A | 8/1992 | Mauze et al. |
| 5,147,186 A | 9/1992 | Buckholtz |
| 5,163,910 A | 11/1992 | Schwartz et al. |
| 5,169,378 A | 12/1992 | Figuera |
| 5,171,212 A | 12/1992 | Buck et al. |
| 5,190,528 A | 3/1993 | Fonger et al. |
| 5,201,679 A | 4/1993 | Velte et al. |
| 5,211,546 A | 5/1993 | Isaacson et al. |
| 5,221,270 A | 6/1993 | Parker |
| 5,234,416 A | 8/1993 | Macaulay et al. |
| 5,290,227 A | 3/1994 | Pasque |
| 5,300,112 A | 4/1994 | Barr |
| 5,312,341 A | 5/1994 | Turi |
| 5,344,443 A | 9/1994 | Palma et al. |
| 5,346,458 A | 9/1994 | Affeld |
| 5,360,317 A | 11/1994 | Clausen et al. |
| 5,376,114 A | 12/1994 | Jarvik |
| 5,393,197 A | 2/1995 | Lemont et al. |
| 5,393,207 A | 2/1995 | Maher et al. |
| 5,405,341 A | 4/1995 | Martin |
| 5,405,383 A | 4/1995 | Barr |
| 5,415,637 A | 5/1995 | Khosravi |
| 5,437,541 A | 8/1995 | Vainrub et al. |
| 5,449,342 A | 9/1995 | Hirose et al. |
| 5,458,459 A | 10/1995 | Hubbard et al. |
| 5,490,763 A | 2/1996 | Abrams et al. |
| 5,505,701 A | 4/1996 | Anaya Fernandez de Lomana |
| 5,527,159 A | 6/1996 | Bozeman, Jr. et al. |
| 5,533,957 A | 7/1996 | Aldea |
| 5,534,287 A | 7/1996 | Lukic |
| 5,554,114 A | 9/1996 | Wallace et al. |
| 5,588,812 A | 12/1996 | Taylor et al. |
| 5,609,574 A | 3/1997 | Kaplan et al. |
| 5,613,935 A | 3/1997 | Jarvik |
| 5,643,226 A | 7/1997 | Cosgrove et al. |
| 5,678,306 A | 10/1997 | Bozeman, Jr. et al. |
| 5,692,882 A | 12/1997 | Bozeman et al. |
| 5,702,418 A | 12/1997 | Ravenscroft |
| 5,704,926 A | 1/1998 | Sutton |
| 5,707,218 A | 1/1998 | Maher et al. |
| 5,722,930 A | 3/1998 | Larson et al. |
| 5,725,513 A | 3/1998 | Ju et al. |
| 5,725,570 A | 3/1998 | Heath |
| 5,730,628 A | 3/1998 | Hawkins |
| 5,735,897 A | 4/1998 | Buirge |
| 5,738,649 A | 4/1998 | Macoviak |
| 5,741,234 A | 4/1998 | Aboul-Hosn |
| 5,741,429 A | 4/1998 | Donadio, III et al. |
| 5,746,709 A | 5/1998 | Rom et al. |
| 5,749,855 A | 5/1998 | Reitan |
| 5,755,784 A | 5/1998 | Jarvik |
| 5,776,111 A | 7/1998 | Tesio |
| 5,776,161 A | 7/1998 | Globerman |
| 5,776,190 A | 7/1998 | Jarvik |
| 5,779,721 A | 7/1998 | Nash |
| 5,807,311 A | 9/1998 | Palestrant |
| 5,814,011 A | 9/1998 | Corace |
| 5,824,070 A | 10/1998 | Jarvik |
| 5,851,174 A | 12/1998 | Jarvik et al. |
| 5,859,482 A | 1/1999 | Crowell et al. |
| 5,868,702 A | 2/1999 | Stevens |
| 5,868,703 A | 2/1999 | Bertolero |
| 5,888,241 A | 3/1999 | Jarvik |
| 5,888,242 A | 3/1999 | Antaki et al. |
| 5,911,685 A | 6/1999 | Siess et al. |
| 5,921,913 A | 7/1999 | Siess |
| 5,941,813 A | 8/1999 | Sievers et al. |
| 5,951,263 A | 9/1999 | Taylor et al. |
| 5,957,941 A | 9/1999 | Ream |
| 5,964,694 A | 10/1999 | Siess et al. |
| 6,007,478 A | 12/1999 | Siess et al. |
| 6,007,479 A | 12/1999 | Rottenberg et al. |
| 6,015,272 A | 1/2000 | Antaki et al. |
| 6,015,434 A | 1/2000 | Yamane |
| 6,018,208 A | 1/2000 | Maher et al. |
| 6,027,863 A | 2/2000 | Donadio, III et al. |
| 6,053,705 A | 4/2000 | Schob et al. |
| 6,056,719 A | 5/2000 | Mickley |
| 6,058,593 A | 5/2000 | Siess |
| 6,059,760 A | 5/2000 | Sandmore et al. |
| 6,068,610 A | 5/2000 | Ellis et al. |
| 6,071,093 A | 6/2000 | Hart |
| 6,083,260 A | 7/2000 | Aboul-Hosn |
| 6,086,527 A | 7/2000 | Talpade |
| 6,086,570 A | 7/2000 | Aboul-Hosn et al. |
| 6,106,494 A | 8/2000 | Saravia et al. |
| 6,113,536 A | 9/2000 | Aboul-Hosn et al. |
| 6,123,659 A | 9/2000 | Le Blanc et al. |
| 6,123,725 A | 9/2000 | Aboul-Hosn |
| 6,132,363 A | 10/2000 | Freed et al. |
| 6,135,943 A | 10/2000 | Yu et al. |
| 6,136,025 A | 10/2000 | Barbut et al. |

(56) References Cited

U.S. PATENT DOCUMENTS

| | | |
|---|---|---|
| 6,139,487 A | 10/2000 | Siess |
| 6,152,704 A | 11/2000 | Aboul-Hosn et al. |
| 6,162,194 A | 12/2000 | Shipp |
| 6,176,822 B1 | 1/2001 | Nix et al. |
| 6,176,848 B1 | 1/2001 | Rau et al. |
| 6,186,665 B1 | 2/2001 | Maher et al. |
| 6,190,304 B1 | 2/2001 | Downey et al. |
| 6,200,260 B1 | 3/2001 | Bolling |
| 6,210,133 B1 | 4/2001 | Aboul-Hosn et al. |
| 6,210,397 B1 | 4/2001 | Aboul-Hosn et al. |
| 6,214,846 B1 | 4/2001 | Elliott |
| 6,217,541 B1 | 4/2001 | Yu |
| 6,227,797 B1 | 5/2001 | Watterson et al. |
| 6,228,063 B1 | 5/2001 | Aboul-Hosn |
| 6,234,960 B1 | 5/2001 | Aboul-Hosn et al. |
| 6,234,995 B1 | 5/2001 | Peacock, III |
| 6,245,007 B1 | 6/2001 | Bedingham et al. |
| 6,245,026 B1 | 6/2001 | Campbell et al. |
| 6,247,892 B1 | 6/2001 | Kazatchkov et al. |
| 6,248,091 B1 | 6/2001 | Voelker |
| 6,254,359 B1 | 7/2001 | Aber |
| 6,254,564 B1 | 7/2001 | Wilk et al. |
| 6,287,319 B1 | 9/2001 | Aboul-Hosn et al. |
| 6,287,336 B1 | 9/2001 | Globerman et al. |
| 6,295,877 B1 | 10/2001 | Aboul-Hosn et al. |
| 6,299,635 B1 | 10/2001 | Frantzen |
| 6,305,962 B1 | 10/2001 | Maher et al. |
| 6,387,037 B1 | 5/2002 | Bolling et al. |
| 6,395,026 B1 | 5/2002 | Aboul-Hosn et al. |
| 6,413,222 B1 | 7/2002 | Pantages et al. |
| 6,422,990 B1 | 7/2002 | Prem |
| 6,425,007 B1 | 7/2002 | Messinger |
| 6,428,464 B1 | 8/2002 | Bolling |
| 6,447,441 B1 | 9/2002 | Yu et al. |
| 6,468,298 B1 | 10/2002 | Pelton |
| 6,503,224 B1 | 1/2003 | Forman et al. |
| 6,508,777 B1 | 1/2003 | Macoviak et al. |
| 6,508,787 B2 | 1/2003 | Erbel et al. |
| 6,517,315 B2 | 2/2003 | Belady |
| 6,517,528 B1 | 2/2003 | Pantages et al. |
| 6,527,699 B1 | 3/2003 | Goldowsky |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | de Blanc et al. |
| 6,565,598 B1 | 5/2003 | Lootz |
| 6,609,883 B2 | 8/2003 | Woodard et al. |
| 6,610,004 B2 | 8/2003 | Viole et al. |
| 6,613,008 B2 | 9/2003 | Aboul-Hosn et al. |
| 6,616,323 B2 | 9/2003 | McGill |
| 6,623,420 B2 | 9/2003 | Reich et al. |
| 6,623,475 B1 | 9/2003 | Siess |
| 6,641,093 B2 | 11/2003 | Coudrais |
| 6,641,558 B1 | 11/2003 | Aboul-Hosn et al. |
| 6,645,241 B1 | 11/2003 | Strecker |
| 6,652,548 B2 | 11/2003 | Evans et al. |
| 6,660,014 B2 | 12/2003 | Demarais et al. |
| 6,673,105 B1 | 1/2004 | Chen |
| 6,692,318 B2 | 2/2004 | McBride |
| 6,709,418 B1 | 3/2004 | Aboul-Hosn et al. |
| 6,716,189 B1 | 4/2004 | Jarvik et al. |
| 6,749,598 B1 | 6/2004 | Keren et al. |
| 6,776,578 B2 | 8/2004 | Belady |
| 6,776,794 B1 | 8/2004 | Hong et al. |
| 6,783,328 B2 | 8/2004 | Lucke et al. |
| 6,790,171 B1 | 9/2004 | Grundeman et al. |
| 6,794,784 B2 | 9/2004 | Takahashi et al. |
| 6,794,789 B2 | 9/2004 | Siess et al. |
| 6,814,713 B2 | 11/2004 | Aboul-Hosn et al. |
| 6,817,836 B2 | 11/2004 | Nose et al. |
| 6,818,001 B2 | 11/2004 | Wulfman et al. |
| 6,860,713 B2 | 3/2005 | Hoover |
| 6,866,625 B1 | 3/2005 | Avre et al. |
| 6,866,805 B2 | 3/2005 | Hong et al. |
| 6,887,215 B2 | 5/2005 | McWeeney |
| 6,889,082 B2 | 5/2005 | Bolling et al. |
| 6,901,289 B2 | 5/2005 | Dahl et al. |
| 6,926,662 B1 | 8/2005 | Aboul-Hosn et al. |
| 6,935,344 B1 | 8/2005 | Aboul-Hosn et al. |
| 6,942,611 B2 | 9/2005 | Siess |
| 6,949,066 B2 | 9/2005 | Bearnson et al. |
| 6,966,748 B2 | 11/2005 | Woodard et al. |
| 6,972,956 B2 | 12/2005 | Franz et al. |
| 6,974,436 B1 | 12/2005 | Aboul-Hosn et al. |
| 6,981,942 B2 | 1/2006 | Khaw et al. |
| 6,984,392 B2 | 1/2006 | Bechert et al. |
| 7,010,954 B2 | 3/2006 | Siess et al. |
| 7,011,620 B1 | 3/2006 | Siess |
| 7,014,417 B2 | 3/2006 | Salomon |
| 7,022,100 B1 | 4/2006 | Aboul-Hosn et al. |
| 7,027,875 B2 | 4/2006 | Siess et al. |
| 7,037,069 B2 | 5/2006 | Arnold et al. |
| 7,070,555 B2 | 7/2006 | Siess |
| 7,122,019 B1 | 10/2006 | Kesten et al. |
| 7,125,376 B2 | 10/2006 | Viole et al. |
| 7,144,365 B2 | 12/2006 | Bolling et al. |
| 7,150,711 B2 | 12/2006 | Nusser et al. |
| 7,160,243 B2 | 1/2007 | Medvedev |
| 7,172,551 B2 | 2/2007 | Leasure |
| 7,175,588 B2 | 2/2007 | Morello |
| 7,229,258 B2 | 6/2007 | Wood et al. |
| 7,241,257 B1 | 7/2007 | Ainsworth et al. |
| 7,262,531 B2 | 8/2007 | Li et al. |
| 7,264,606 B2 | 9/2007 | Jarvik et al. |
| 7,267,667 B2 | 9/2007 | Houde et al. |
| 7,284,956 B2 | 10/2007 | Nose et al. |
| 7,288,111 B1 | 10/2007 | Holloway et al. |
| 7,290,929 B2 | 11/2007 | Smith et al. |
| 7,329,236 B2 | 2/2008 | Keren et al. |
| 7,331,921 B2 | 2/2008 | Viole et al. |
| 7,335,192 B2 | 2/2008 | Keren et al. |
| 7,341,570 B2 | 3/2008 | Keren et al. |
| 7,381,179 B2 | 6/2008 | Aboul-Hosn et al. |
| 7,393,181 B2 | 7/2008 | McBride et al. |
| 7,469,716 B2 | 12/2008 | Parrino et al. |
| 7,491,163 B2 | 2/2009 | Viole et al. |
| 7,534,258 B2 | 5/2009 | Gomez |
| 7,605,298 B2 | 10/2009 | Bechert et al. |
| 7,619,560 B2 | 11/2009 | Penna |
| 7,633,193 B2 | 12/2009 | Masoudipour et al. |
| 7,645,225 B2 | 1/2010 | Medvedev et al. |
| 7,657,324 B2 | 2/2010 | Westlund et al. |
| 7,682,673 B2 | 3/2010 | Houston et al. |
| 7,731,675 B2 | 6/2010 | Aboul-Hosn et al. |
| 7,736,296 B2 | 6/2010 | Siess et al. |
| 7,758,521 B2 | 7/2010 | Morris et al. |
| 7,766,892 B2 | 8/2010 | Keren et al. |
| 7,780,628 B1 | 8/2010 | Keren et al. |
| 7,785,246 B2 | 8/2010 | Aboul-Hosn et al. |
| 7,811,279 B2 | 10/2010 | John |
| 7,819,833 B2 | 10/2010 | Ainsworth et al. |
| 7,820,205 B2 | 10/2010 | Takakusagi et al. |
| 7,828,710 B2 | 11/2010 | Shifflette |
| 7,841,976 B2 | 11/2010 | McBride et al. |
| 7,878,967 B1 | 2/2011 | Khanal |
| 7,918,828 B2 | 4/2011 | Lundgaard et al. |
| 7,927,068 B2 | 4/2011 | McBride et al. |
| 7,935,102 B2 | 5/2011 | Breznock et al. |
| 7,942,804 B2 | 5/2011 | Khaw |
| 7,942,844 B2 | 5/2011 | Moberg et al. |
| 7,955,365 B2 | 6/2011 | Doty |
| 7,993,259 B2 | 8/2011 | Kang et al. |
| 7,998,054 B2 | 8/2011 | Bolling |
| 7,998,190 B2 | 8/2011 | Gharib et al. |
| 8,012,079 B2 | 9/2011 | Delgado |
| 8,025,647 B2 | 9/2011 | Siess et al. |
| 8,079,948 B2 | 12/2011 | Shifflette |
| 8,110,267 B2 | 2/2012 | Houston et al. |
| 8,114,008 B2 | 2/2012 | Hidaka et al. |
| 8,123,669 B2 | 2/2012 | Siess et al. |
| 8,177,703 B2 | 5/2012 | Smith et al. |
| 8,206,350 B2 | 6/2012 | Mann et al. |
| 8,209,015 B2 | 6/2012 | Glenn |
| 8,235,943 B2 | 8/2012 | Breznock et al. |

(56) References Cited

U.S. PATENT DOCUMENTS

| | | |
|---|---|---|
| 8,236,044 B2 | 8/2012 | Robaina |
| 8,255,050 B2 | 8/2012 | Mohl |
| 8,257,312 B2 | 9/2012 | Duffy |
| 8,262,619 B2 | 9/2012 | Chebator et al. |
| 8,277,470 B2 | 10/2012 | Demarais et al. |
| 8,317,715 B2 | 11/2012 | Belleville et al. |
| 8,329,913 B2 | 12/2012 | Murata et al. |
| 8,348,991 B2 | 1/2013 | Weber et al. |
| 8,364,278 B2 | 1/2013 | Pianca et al. |
| 8,376,707 B2 | 2/2013 | McBride et al. |
| 8,382,818 B2 | 2/2013 | Davis et al. |
| 8,388,565 B2 | 3/2013 | Shifflette |
| 8,409,128 B2 | 4/2013 | Ferrari |
| 8,414,645 B2 | 4/2013 | Dwork et al. |
| 8,439,859 B2 | 5/2013 | Pfeffer et al. |
| 8,449,443 B2 | 5/2013 | Rodefeld |
| 8,485,961 B2 | 7/2013 | Campbell et al. |
| 8,489,190 B2 | 7/2013 | Pfeffer et al. |
| 8,535,211 B2 | 9/2013 | Campbell et al. |
| 8,540,615 B2 | 9/2013 | Aboul-Hosn et al. |
| 8,545,379 B2 | 10/2013 | Marseille et al. |
| 8,545,380 B2 | 10/2013 | Farnan et al. |
| 8,579,858 B2 | 11/2013 | Reitan |
| 8,585,572 B2 | 11/2013 | Mehmanesh |
| 8,591,393 B2 | 11/2013 | Walters et al. |
| 8,597,170 B2 | 12/2013 | Walters et al. |
| 8,617,239 B2 | 12/2013 | Reitan |
| 8,684,904 B2 | 4/2014 | Campbell et al. |
| 8,690,749 B1 | 4/2014 | Nunez |
| 8,721,516 B2 | 5/2014 | Scheckel |
| 8,721,517 B2 | 5/2014 | Zeng et al. |
| 8,727,959 B2 | 5/2014 | Reitan et al. |
| 8,734,331 B2 | 5/2014 | Evans et al. |
| 8,784,441 B2 | 7/2014 | Rosenbluth et al. |
| 8,790,236 B2 | 7/2014 | LaRose et al. |
| 8,795,576 B2 | 8/2014 | Tao et al. |
| 8,801,590 B2 | 8/2014 | Mohl |
| 8,814,776 B2 | 8/2014 | Hastie et al. |
| 8,814,933 B2 | 8/2014 | Siess |
| 8,849,398 B2 | 9/2014 | Evans |
| 8,944,748 B2 | 2/2015 | Liebing |
| 8,992,406 B2 | 3/2015 | Corbett |
| 8,998,792 B2 | 4/2015 | Scheckel |
| 9,028,216 B2 | 5/2015 | Schumacher et al. |
| 9,162,017 B2 | 10/2015 | Evans et al. |
| 9,308,302 B2 | 4/2016 | Zeng |
| 9,327,067 B2 | 5/2016 | Zeng et al. |
| 2002/0107506 A1 | 8/2002 | McGuckin, Jr. et al. |
| 2003/0018380 A1 | 1/2003 | Craig et al. |
| 2003/0205233 A1 | 11/2003 | Aboul-Hosn et al. |
| 2003/0208097 A1 | 11/2003 | Aboul-Hosn et al. |
| 2003/0231959 A1 | 12/2003 | Snider |
| 2005/0049696 A1 | 3/2005 | Siess et al. |
| 2005/0085683 A1 | 4/2005 | Bolling et al. |
| 2005/0113631 A1 | 5/2005 | Bolling et al. |
| 2005/0137680 A1 | 6/2005 | Ortiz et al. |
| 2005/0165269 A9 | 7/2005 | Aboul-Hosn et al. |
| 2005/0250975 A1 | 11/2005 | Carrier et al. |
| 2006/0018943 A1 | 1/2006 | Bechert et al. |
| 2006/0058869 A1 | 3/2006 | Olson et al. |
| 2006/0063965 A1 | 3/2006 | Aboul-Hosn et al. |
| 2006/0089521 A1 | 4/2006 | Chang |
| 2006/0155158 A1 | 7/2006 | Aboul-Hosn |
| 2006/0264695 A1 | 11/2006 | Viole et al. |
| 2006/0270894 A1 | 11/2006 | Viole et al. |
| 2007/0100314 A1 | 5/2007 | Keren et al. |
| 2008/0004645 A1* | 1/2008 | To .............. A61B 17/320758 606/159 |
| 2008/0103442 A1 | 5/2008 | Kesten et al. |
| 2008/0103516 A1 | 5/2008 | Wulfman et al. |
| 2008/0119943 A1 | 5/2008 | Armstrong et al. |
| 2008/0132748 A1 | 6/2008 | Shifflete |
| 2008/0167679 A1 | 7/2008 | Papp |
| 2008/0275290 A1 | 11/2008 | Viole et al. |
| 2009/0018567 A1 | 1/2009 | Escudero et al. |
| 2009/0024085 A1 | 1/2009 | To et al. |
| 2009/0112312 A1 | 4/2009 | LaRose et al. |
| 2009/0118567 A1 | 5/2009 | Siess |
| 2009/0182188 A1 | 7/2009 | Marseille et al. |
| 2009/0234378 A1 | 9/2009 | Escudero et al. |
| 2010/0030186 A1 | 2/2010 | Stivland |
| 2010/0041939 A1 | 2/2010 | Siess |
| 2010/0127871 A1 | 5/2010 | Pontin |
| 2010/0210895 A1 | 8/2010 | Aboul-Hosn et al. |
| 2010/0268017 A1 | 10/2010 | Siess |
| 2010/0274330 A1 | 10/2010 | Burwell et al. |
| 2010/0286791 A1 | 11/2010 | Goldsmith |
| 2011/0071338 A1 | 3/2011 | McBride et al. |
| 2011/0076439 A1 | 3/2011 | Zeilon |
| 2011/0152906 A1 | 6/2011 | Escudero et al. |
| 2011/0152907 A1 | 6/2011 | Escudero et al. |
| 2011/0237863 A1 | 9/2011 | Ricci et al. |
| 2012/0004495 A1 | 1/2012 | Bolling |
| 2012/0029265 A1 | 2/2012 | LaRose et al. |
| 2012/0142994 A1 | 6/2012 | Toellner |
| 2012/0172654 A1 | 7/2012 | Bates |
| 2012/0178986 A1 | 7/2012 | Campbell et al. |
| 2012/0224970 A1 | 9/2012 | Schumacher et al. |
| 2012/0226097 A1 | 9/2012 | Smith et al. |
| 2012/0245404 A1 | 9/2012 | Smith et al. |
| 2012/0265002 A1 | 10/2012 | Roehn et al. |
| 2013/0041202 A1 | 2/2013 | Toellner |
| 2013/0053622 A1 | 2/2013 | Corbett |
| 2013/0053623 A1 | 2/2013 | Evans et al. |
| 2013/0066140 A1 | 3/2013 | McBride et al. |
| 2013/0085318 A1 | 4/2013 | Toellner |
| 2013/0096364 A1 | 4/2013 | Reichenbach et al. |
| 2013/0103063 A1 | 4/2013 | Escudero et al. |
| 2013/0106212 A1 | 5/2013 | Nakazumi et al. |
| 2013/0129503 A1 | 5/2013 | McBride et al. |
| 2013/0138205 A1 | 5/2013 | Kushwaha et al. |
| 2013/0209292 A1 | 8/2013 | Baykut et al. |
| 2013/0237744 A1 | 9/2013 | Pfeffer et al. |
| 2013/0303969 A1 | 11/2013 | Keenan et al. |
| 2013/0303970 A1 | 11/2013 | Keenan et al. |
| 2013/0331639 A1 | 12/2013 | Campbell et al. |
| 2013/0345492 A1 | 12/2013 | Pfeffer et al. |
| 2014/0005467 A1 | 1/2014 | Farnan et al. |
| 2014/0010686 A1 | 1/2014 | Tanner et al. |
| 2014/0012065 A1 | 1/2014 | Fitzgerald et al. |
| 2014/0088455 A1 | 3/2014 | Christensen et al. |
| 2014/0148638 A1 | 5/2014 | LaRose et al. |
| 2014/0163664 A1 | 6/2014 | Goldsmith |
| 2014/0275725 A1 | 9/2014 | Schenck et al. |
| 2014/0275726 A1 | 9/2014 | Zeng et al. |
| 2014/0301822 A1 | 10/2014 | Scheckel |
| 2015/0025558 A1 | 1/2015 | Wulfman et al. |
| 2015/0031936 A1 | 1/2015 | LaRose et al. |
| 2015/0051435 A1 | 2/2015 | Siess et al. |
| 2015/0080743 A1 | 3/2015 | Siess |
| 2015/0087890 A1 | 3/2015 | Spanier et al. |
| 2015/0141739 A1 | 5/2015 | Hsu et al. |
| 2015/0151032 A1 | 6/2015 | Voskoboynikov |
| 2015/0209498 A1 | 7/2015 | Franono et al. |
| 2015/0250935 A1 | 9/2015 | Anderson et al. |
| 2015/0290372 A1 | 10/2015 | Muller et al. |
| 2016/0184500 A1 | 6/2016 | Zeng |

FOREIGN PATENT DOCUMENTS

| | | |
|---|---|---|
| EP | 1 207 934 | 5/2002 |
| EP | 1 591 079 A1 | 11/2005 |
| EP | 2 263 732 | 12/2010 |
| EP | 2 298 374 A1 | 3/2011 |
| FR | 2267800 | 4/1974 |
| GB | 2 239 675 A | 7/1991 |
| JP | S48-23295 | 3/1973 |
| JP | 06-114101 | 4/1994 |
| JP | 10-099447 | 4/1998 |
| TW | 500877 | 9/2002 |
| WO | WO 89/05164 | 6/1989 |
| WO | WO 97/15228 | 5/1997 |
| WO | WO 97/37697 | 10/1997 |
| WO | WO 00/12148 | 3/2000 |

(56) References Cited

FOREIGN PATENT DOCUMENTS

| WO | WO 00/19097 | 4/2000 |
|---|---|---|
| WO | WO 00/43062 | 7/2000 |
| WO | WO 00/61207 | 10/2000 |
| WO | WO 00/69489 | 11/2000 |
| WO | WO 01/17581 A2 | 3/2001 |
| WO | WO 01/24867 | 4/2001 |
| WO | WO 02/070039 | 9/2002 |
| WO | WO 03/103745 | 12/2003 |
| WO | WO 2005/089674 | 9/2005 |
| WO | WO 2005/123158 | 12/2005 |
| WO | WO 2009/073037 | 6/2009 |
| WO | WO 2009/076460 A2 | 6/2009 |
| WO | WO 2010/127871 | 11/2010 |
| WO | WO 2010/133567 | 11/2010 |
| WO | WO 2010/149393 | 12/2010 |
| WO | WO 2011/035926 | 3/2011 |
| WO | WO 2011/035929 | 3/2011 |
| WO | WO 2011/039091 A1 | 4/2011 |
| WO | WO 2011/076439 | 6/2011 |
| WO | WO 2011/089022 | 7/2011 |
| WO | WO 2012/007140 | 1/2012 |
| WO | WO 2012/007141 | 1/2012 |
| WO | WO 2013/160407 A1 | 10/2013 |
| WO | WO 2014/019274 A1 | 2/2014 |

OTHER PUBLICATIONS

Abiomed—Recovering Hearts. Saving Lives., Impella 2.5 System, Instructions for Use, Jul. 2007, in 86 sheets.
Aboul-Hosn et al., "The Hemopump: Clinical Results and Future Applications", Assisted Circulation 4, 1995, in 14 pages.
Barras et al., "Nitinol-Its Use in Vascular Surgery and Other Applications," Eur. J. Vasc. Endovasc. Surg., 2000, pp. 564-569; vol. 19.
Biscarini et al., "Enhanced Nitinol Properties for Biomedical Applications," Recent Patents on Biomedical Engineering, 2008, pp. 180-196, vol. 1(3).
Cardiovascular Diseases (CVDs) Fact Sheet No. 317; World Health Organization [Online], Sep. 2011. http://www.who.int/mediacentre/factsheets/fs317/en/index.html, accessed on Aug. 29, 2012.
Compendium of Technical and Scientific Information for the HEMOPUMP Temporary Cardiac Assist System, Johnson & Johnson Interventional Systems, 1988, in 15 pages.
Dekker et al., "Efficacy of a New Intraaortic Propeller Pump vs the Intraaortic Balloon Pump*, An Animal Study", Chest, Jun. 2003, vol. 123, No. 6, pp. 2089-2095.
Duerig et al., "An Overview of Nitinol Medical Applications," Materials Science Engineering, 1999, pp. 149-160; vol. A273.
European Search Report received in European Patent Application No. 05799883.3, dated May 10, 2011, in 4 pages.
Extended European Search Report received in European Patent Application No. 07753903.9, dated Oct. 8, 2012, in 7 pages.
Extended European Search Report received in European Patent Application No. 13813687.4, dated Feb. 24, 2016, in 6 pages.
Extended European Search Report received in European Patent Application No. 13813867.2, dated Feb. 26, 2016, in 6 pages.
Federal and Drug Administration 510(k) Summary for Predicate Device IMPELLA 2.5 (K112892), prepared Sep. 5, 2012.
Grech, "Percutaneous Coronary Intervention. I: History and Development," BMJ., May 17, 2003, pp. 1080-1082, vol. 326.
Hsu et al., "Review of Recent Patents on Foldable Ventricular Assist Devices," Recent Patents on Biomedical Engineering, 2012, pp. 208-222, vol. 5.
Ide et al., "Evaluation of the Pulsatility of a New Pulsatile Left Ventricular Assist Device-the Integrated Cardioassist Catheter-in Dogs," J. of Thorac and Cardiovasc Sur, Feb. 1994, pp. 569-0575, vol. 107(2).
Ide et al., "Hemodynamic Evaluation of a New Left Ventricular Assist Device: An Integrated Cardioassist Catheter as a Pulsatile Left Ventricle-Femoral Artery Bypass," Blackwell Scientific Publications, Inc., 1992, pp. 286-290, vol. 16(3).
Impella CP®—Instructions for Use & Clinical Reference Manual (United States only), Abiomed, Inc., Jul. 2014, 148 pages, www.abiomed.com.
Impella LD®—with the Impella® Controller—Circulatory Support System—Instructions for Use & Clinical Reference Manual (United States only), Abiomed, Inc., Sep. 2010, 132 pages, www.abiomed.com.
International Preliminary Examination Report received in International Patent Application No. PCT/US2003/04853, dated Jul. 26, 2004, in 5 pages.
International Preliminary Examination Report received in International Patent Application No. PCT/US2003/04401, dated May 18, 2004, in 4 pages.
International Preliminary Report on Patentability and Written Opinion of the International Searching Authority received in International Patent Application No. PCT/US2005/033416, dated Mar. 20, 2007, in 7 pages.
International Preliminary Report on Patentability and Written Opinion of the International Searching Authority received in International Patent Application No. PCT/US2007/007313, dated Sep. 23, 2008, in 6 pages.
International Preliminary Report on Patentability and Written Opinion received in International Patent Application No. PCT/US2014/020878, dated Sep. 15, 2015, in 8 pages.
International Search Report and Written Opinion received in International Patent Application No. PCT/US2005/033416, dated Dec. 11, 2006, in 8 pages.
International Search Report and Written Opinion received in International Patent Application No. PCT/US2007/007313, dated Mar. 4, 2008, in 6 pages.
International Search Report and Written Opinion received in International Patent Application No. PCT/US2012/020382, dated Jul. 31, 2012, in 11 pages.
International Search Report and Written Opinion received in International Patent Application No. PCT/US2012/020369, dated Jul. 30, 2012, in 10 pages.
International Search Report and Written Opinion received in International Patent Application No. PCT/US2012/020553, dated Aug. 17, 2012, in 8 pages.
International Search Report and Written Opinion received in International Patent Application No. PCT/US2012/020383, dated Aug. 17, 2012; in 9 pages.
International Search Report and Written Opinion received in International Patent Application No. PCT/US2013/040798, dated Aug. 21, 2013, in 16 pages.
International Search Report and Written Opinion received in International Patent Application No. PCT/US2013/040799, dated Aug. 21, 2013, in 19 pages.
International Search Report and Written Opinion received in International Patent Application No. PCT/US2013/040809, dated Sep. 2, 2013, in 25 pages.
International Search Report and Written Opinion received in International Patent Application No. PCT/US2013/048332, dated Oct. 16, 2013, in 17 pages.
International Search Report and Written Opinion received in International Patent Application No. PCT/US2013/048343, dated Oct. 11, 2013, in 15 pages.
International Search Report and Written Opinion received in International Patent Application No. PCT/US2014/020878, dated May 7, 2014, in 13 pages.
International Search Reort and Written Opinion received in International Patent Application No. PCT/US2015/026013, dated Jul. 8, 2015, in 12 pages.
International Search Report and Written Opinion received in International Patent Application No. PCT/US2015/026014, dated Jul. 15, 2015, in 13 pages.
International Search Report and Written Opinion received in International Patent Application No. PCT/US2015/026025, dated Jul. 20, 2015, in 12 pages.

(56) References Cited

OTHER PUBLICATIONS

International Search Report and Written Opinion received in International Patent Application No. PCT/US2015/025959, dated Aug. 28, 2015, in 16 pages.
International Search Report and Written Opinion received in International Patent Application No. PCT/US2015/025960, dated Sep. 3, 2015, in 15 pages.
International Search Report and Written Opinion received in International Patent Application No. PCT/US2015/045370, dated Nov. 18, 2015, in 12 pages.
International Search Report and Written Opinion received in International Patent Application No. PCT/US2016/014371, dated May 2, 2016, in 18 pages.
International Search Report and Written Opinion received in International Patent Application No. PCT/US2016/014391, dated May 2, 2016, in 17 pages.
International Search Report received in International Patent Application No. PCT/US2003/004401, dated Nov. 10, 2003, in 9 pages.
International Search Report received in International Patent Application No. PCT/US2003/004853, dated Jul. 3, 2003, in 3 pages.
International Search Report Written Opinion received in International Patent Application No. PCT/US2010/040847, dated Dec. 14, 2010, in 17 pages.
JOMED Reitan Catheter Pump RCP, Percutaneous Circulatory Support, in 10 pages, believed to be published prior to Oct. 15, 2003.
JOMED Reitan Catheter Pump RCP, Feb. 18, 2003, in 4 pages.
Krishnamani et al., "Emerging Ventricular Assist Devices for Long-Term Cardiac Support," National Review, Cardiology, Feb. 2010, pp. 71-76, vol. 7.
Kunst et al., "Integrated unit for programmable control of the 21F Hemopump and registration of physiological signals," Medical & Biological Engineering & Computing, Nov. 1994, pp. 694-696.
Mihaylov et al., "Development of a New Introduction Technique for the Pulsatile Catheter Pump," Artificial Organs, 1997, pp. 425-427; vol. 21(5).
Mihaylov et al., "Evaluation of the Optimal Driving Mode During Left Ventricular Assist with Pulsatile Catheter Pump in Calves," Artificial Organs, 1999, pp. 1117-1122; vol. 23(12).
Minimally Invasive Cardiac Assist JOMED Catheter PumpTM, in 6 pages, believed to be published prior to Jun. 16, 1999.
Morgan, "Medical Shape Memory Alloy Applications—The Market and its Products," Materials Science and Engineering, 2004, pp. 16-23, vol. A 378.
Morsink et al., "Numerical Modelling of Blood Flow Behaviour in the Valved Catheter of the PUCA-Pump, a LVAD," The International Journal of Artificial Organs, 1997, pp. 277-284; vol. 20(5).
Nishimura et al, "The Enabler Cannula Pump: A Novel Circulatory Support System," The International Journal of Artificial Organs, 1999, pp. 317-323; vol. 22(5).
Nullity Action against the owner of the German part DE 50 2007 005 015.6 of European patent EP 2 047 872 B1, dated Jul. 13, 2015, in 61 pages.
Petrini et al., "Biomedical Applications of Shape Memory Alloys," Journal of Metallurgy, 2011, pp. 1-15.
Raess et al., "Impella 2.5," J. Cardiovasc. Transl. Res., 2009, pp. 168-172, vol. 2(2).
Rakhorst et al., "In Vitro Evaluation of the Influence of Pulsatile Intraventricular Pumping on Ventricular Pressure Patterns," Artificial Organs, 1994, pp. 494-499, vol. 18(7).
Reitan, Evaluation of a New Percutaneous Cardiac Assist Device, Department of Cardiology, Faculty of Medicine, Lund University, Sweden, 2002, in 172 pages.
Reitan et al., "Hemodynamic Effects of a New Percutaneous Circulatory Support Device in a Left Ventricular Failure Model," ASAIO Journal, 2003, pp. 731-736, vol. 49.
Reitan et al., "Hydrodynamic Properties of a New Percutaneous Intra-Aortic Axial Flow Pump," ASAIO Journal 2000, pp. 323-328.
Rothman, "The Reitan Catheter Pump: A New Versatile Approach for Hemodynamic Support", London Chest Hospital Barts & The London NHS Trust, Oct. 22-27, 2006 (TCT 2006: Transcatheter Cardiovascular Therapeutics 18th Annual Scientific Symposium, Final Program), in 48 pages.
Schmitz-Rode et al., "An Expandable Percutaneous Catheter Pump for Left Ventricular Support," Journal of the American College of Cardiology, 2005, pp. 1856-1861, vol. 45(11).
Shabari et al., "Improved Hemodynamics with a Novel Miniaturized Intra-Aortic Axial Flow Pump in a Porcine Model of Acute Left Ventricular Dysfunction," ASAIO Journal, 2013, pp. 240-245; vol. 59.
Sharony et al, "Cardiopulmonary Support and Physiology—The Intra-Aortic Cannula Pump: A Novel Assist Device for the Acutely Failing Heart," The Journal of Thoracic and Cardiovascular Surgery, Nov. 1992, pp. 924-929, vol. 118(5).
Sharony et al., "Right Heart Support During Off-Pump Coronary Artery Surgery—A Multi-Center Study," The Heart Surgery Forum, 2002, pp. 13-16, vol. 5(1).
Sieβ et al., "Hydraulic refinement of an intraarterial microaxial blood pump", The International Journal of Artificial Organs, 1995, vol. 18, No. 5, pp. 273-285.
Sieβ, "Systemanalyse and Entwicklung intravasaler Rotationspumpen zur Herzunterstützung", Helmholtz-Institut fur Blomedixinische Technik an der RWTH Aachen, Jun. 24, 1998, in 105 pages.
Siess et al., "Basic design criteria for rotary blood pumps," H. Masuda, Rotary Blood Pumps, Springer, Japan, 2000, pp. 69-83.
Siess et al., "Concept, realization, and first in vitro testing of an intraarterial microaxial blood pump," Artificial Organs, 1995, pp. 644-652, vol. 19, No. 7, Blackwell Science, Inc., Boston, International Society for Artificial Organs.
Siess et al., "From a lab type to a product: A retrospective view on Impella's assist technology," Artificial Organs, 2001, pp. 414-421, vol. 25, No. 5, Blackwell Science, Inc., International Society for Artificial Organs.
Siess et al., "System analysis and development of intravascular rotation pumps for cardiac assist," Dissertation, Shaker Verlag, Aachen, 1999, 39 pages.
Smith et al., "First-In-Man Study of the Reitan Catheter Pump for Circulatory Support in Patients Undergoing High-Risk Percutaneous Coronary Intervention," Catheterization and Cardiovascular Interventions, 2009, pp. 859-865, vol. 73(7).
Sokolowski et al., "Medical Applications of Shape Memory Polymers," Biomed. Mater. 2007, pp. S23-S27, vol. 2.
"Statistical Analysis and Clinical Experience with the Recover® Pump Systems", Impella CardioSystems GmbH, Sep. 2005, 2 sheets.
Stoeckel et al., "Self-Expanding Nitinol Stents—Material and Design Considerations," European Radiology, 2003, in 13 sheets.
Stolinski et al., "The heart-pump interaction: effects of a microaxial blood pump," International Journal of Artificial Organs, 2002, pp. 1082-1088, vol. 25, Issue 11.
Supplemental European Search Report received from the European Patent Office in EP Application No. EP 05799883 dated Mar. 19, 2010, 3 pages.
Takagaki et al., "A Novel Miniature Ventricular Assist Device for Hemodynamic Support," ASAIO Journal, 2001, pp. 412-416; vol. 47.
Throckmorton et al., "Flexible Impeller Blades in an Axial Flow Pump for Intravascular Cavopulmonary Assistance of the Fontan Physiology," Cardiovascular Engineering and Technology, Dec. 2010, pp. 244-255, vol. 1(4).
Throckmorton et al., "Uniquely shaped cardiovascular stents enhance the pressure generation of intravascular blood pumps," The Journal of Thoracic and Cardiovascular Surgery, Sep. 2012, pp. 704-709, vol. 133, No. 3.
Verkerke et al., "Numerical Simulation of the PUCA Pump, A Left Ventricular Assist Device," Abstracts of the XIXth ESAO Congress, The International Journal of Artificial Organs, 1992, p. 543, vol. 15(9).
Verkerke et al., "Numerical Simulation of the Pulsating Catheter Pump: A Left Ventricular Assist Device," Artificial Organs, 1999, pp. 924-931, vol. 23(10).

(56) References Cited

OTHER PUBLICATIONS

Verkerke et al., "The PUCA Pump: A Left Ventricular Assist Device," Artificial Organs, 1993, pp. 365-368, vol. 17(5).
Wampler et al., "The Sternotomy Hemopump, A Second Generation Intraarterial Ventricular Assist Device," ASAIO Journal, 1993, pp. M218-M223, vol. 39.
Weber et al., "Principles of Impella Cardiac Support," Supplemental to Cardiac Interventions Today, Aug./Sep. 2009.
Written Opinion received in International Patent Application No. PCT/US2003/04853, dated Feb. 25, 2004, 5 pages.
International Search Report and Written Opinion received in International Patent Application No. PCT/US2016/014379, dated Jul. 25, 2016, in 19 pages.

* cited by examiner

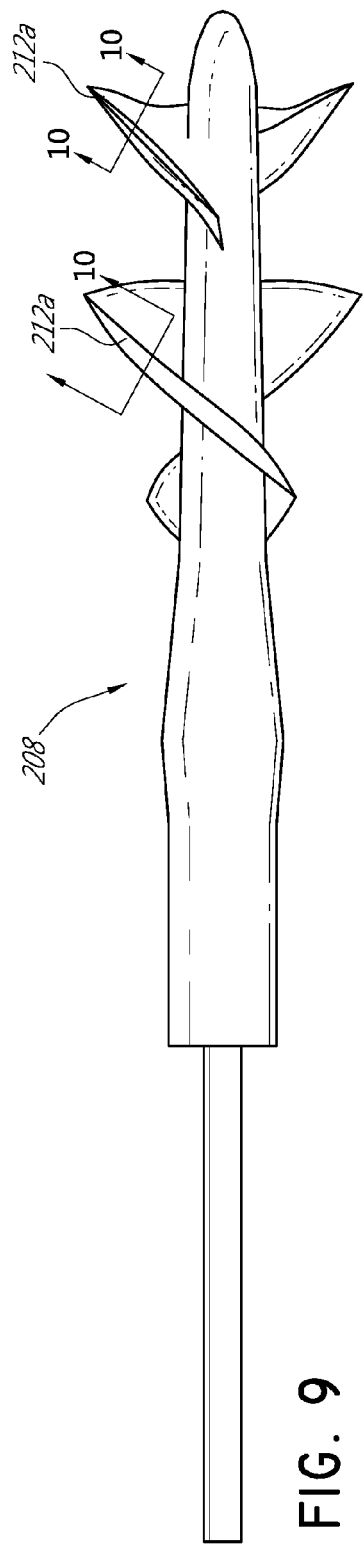
FIG. 9
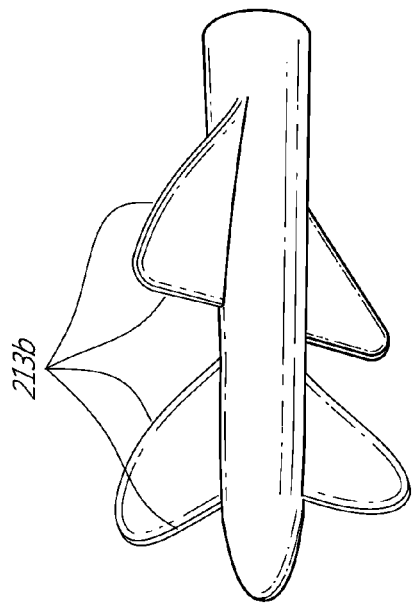
FIG. 9A
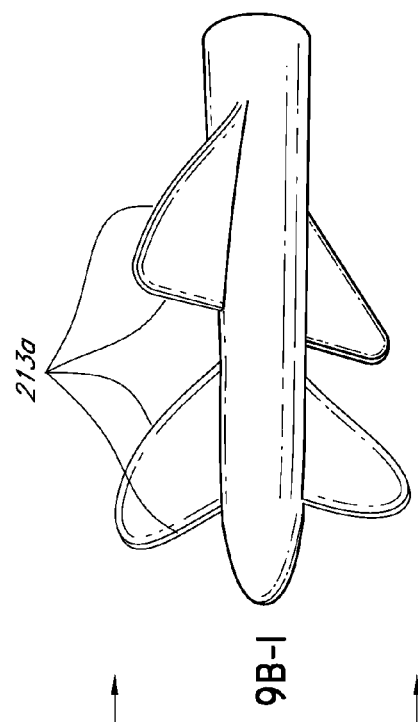
FIG. 9B-I

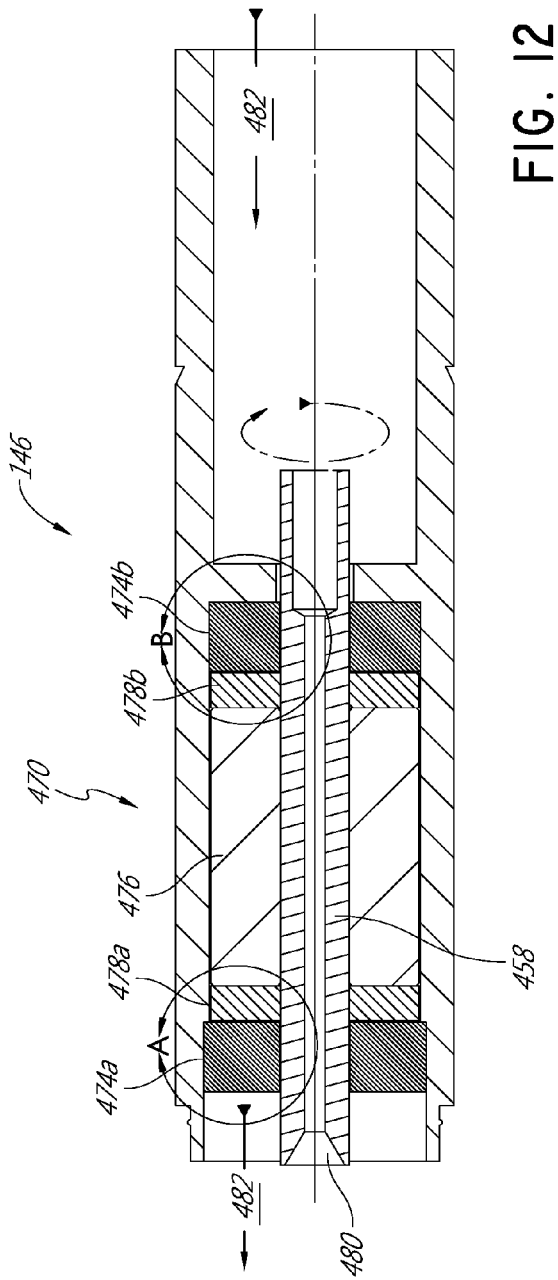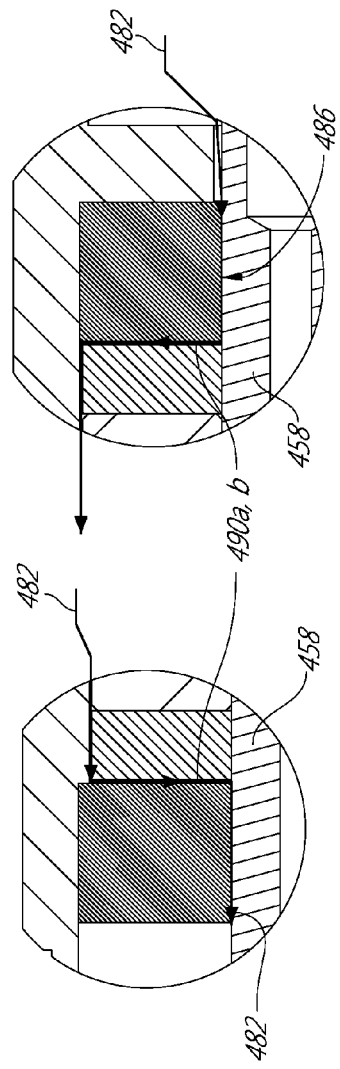

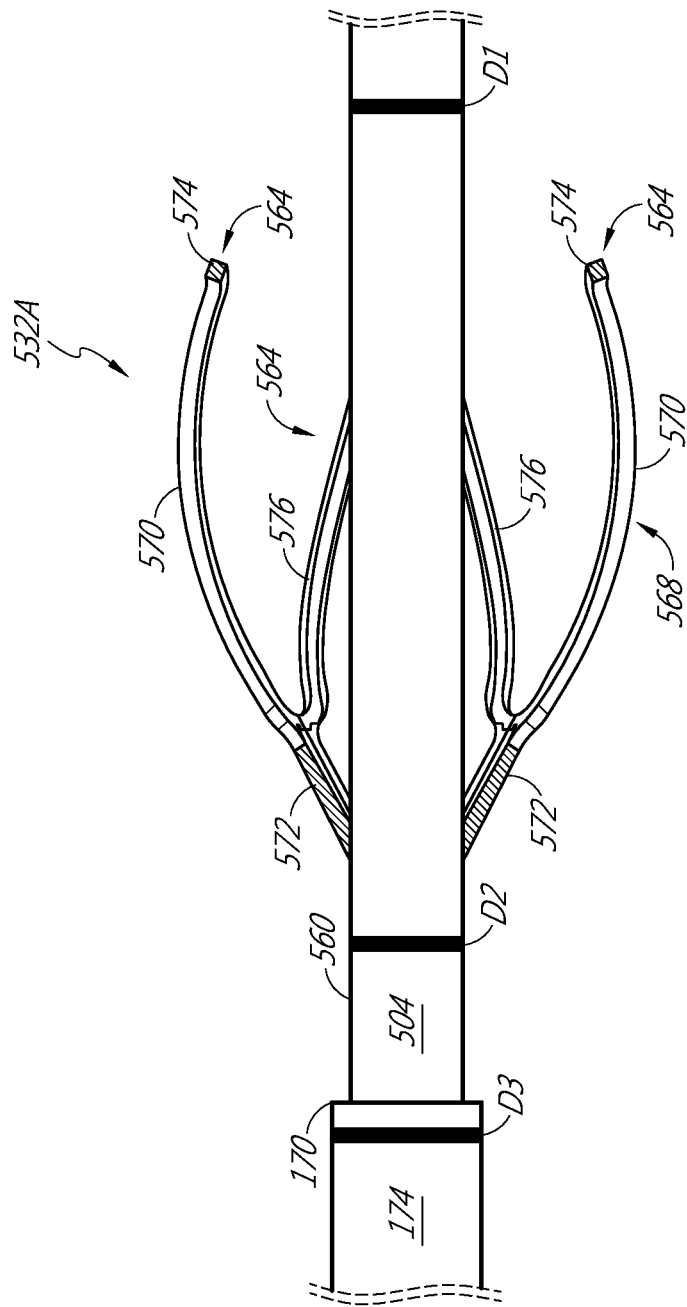

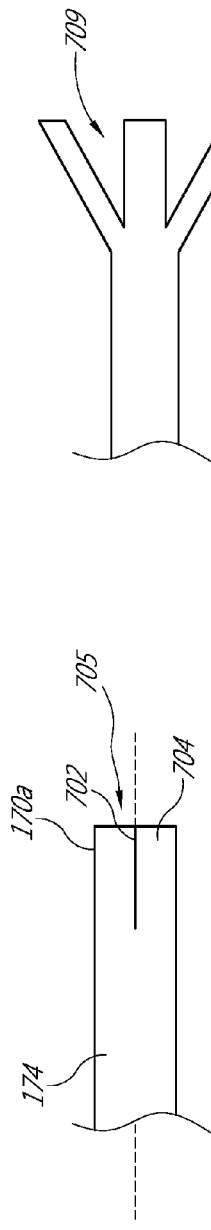
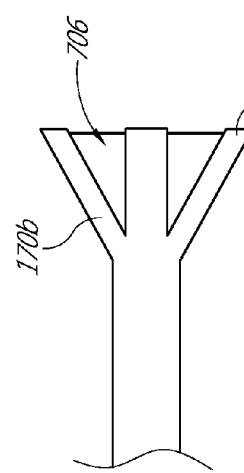
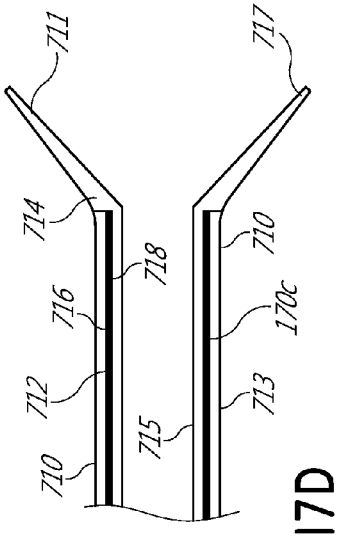
FIG. 17A
FIG. 17B
FIG. 17C
FIG. 17D

CATHETER PUMP WITH POSITIONING BRACE

CROSS-REFERENCE TO RELATED APPLICATIONS

This application claims priority to U.S. Provisional Patent Application No. 62/148,420, filed Apr. 16, 2015, the entire contents of which are incorporated by reference herein in their entirety and for all purposes.

BACKGROUND OF THE INVENTION

Field of the Invention

This application is directed to a catheter pump for mechanical circulatory support of a heart, and related components, systems and methods. In particular, this application is directed to structures and methods for positioning, e.g., by bracing, portions of such pumps in the vasculature and heart chambers.

Description of the Related Art

Heart disease is a major health problem that has high mortality rate. Physicians increasingly use mechanical circulatory support systems for treating heart failure. The treatment of acute heart failure requires a device that can provide support to the patient quickly. Physicians desire treatment options that can be deployed quickly and minimally-invasively.

Intra-aortic balloon pumps (IABP) are currently the most common type of circulatory support devices for treating acute heart failure. IABPs are commonly used to treat heart failure, such as to stabilize a patient after cardiogenic shock, during treatment of acute myocardial infarction (MI) or decompensated heart failure, or to support a patient during high risk percutaneous coronary intervention (PCI). Circulatory support systems may be used alone or with pharmacological treatment.

In a conventional approach, an IABP is positioned in the aorta and actuated in a counterpulsation fashion to provide partial support to the circulatory system. More recently minimally-invasive rotary blood pump have been developed in an attempt to increase the level of potential support (i.e., higher flow). A rotary blood pump is typically inserted into the body and connected to the cardiovascular system, for example, to the left ventricle and the ascending aorta to assist the pumping function of the heart. Other known applications pumping venous blood from the right ventricle to the pulmonary artery for support of the right side of the heart. An aim of acute circulatory support devices is to reduce the load on the heart muscle for a period of time, to stabilize the patient prior to heart transplant or for continuing support.

There is a need for improved mechanical circulatory support devices for treating acute heart failure. Fixed cross-section ventricular assist devices designed to provide near full heart flow rate are either too large to be advanced percutaneously (e.g., through the femoral artery without a cutdown) or provide insufficient flow.

Expandable percutaneous pumps have also been developed. An important variable in expandable percutaneous pumps is the gap between the tip of one or more blades of a rotatable impeller and a cannula wall within which the impeller operates. Variation in the tip gap affects pumping performance and pump durability.

There is a need for a pump with improved performance and clinical outcomes. There is a need for a pump that can provide elevated flow rates with reduced risk of hemolysis and thrombosis. There is a need for a pump that can be inserted minimally-invasively and provide sufficient flow rates for various indications while reducing the risk of major adverse events. In one aspect, there is a need for a heart pump that can be placed minimally-invasively, for example, through a 15 FR or 12 FR incision. In one aspect, there is a need for a heart pump that can provide an average flow rate of 4 Lpm or more during operation, for example, at 62 mmHg of head pressure. While the flow rate of a rotary pump can be increased by rotating the impeller faster, higher rotational speeds are known to increase the risk of hemolysis, which can lead to adverse outcomes and in some cases death. Accordingly, in one aspect, there is a need for a pump that can provide sufficient flow at significantly reduced rotational speeds. These and other problems are overcome by the inventions described herein.

Further, there is a need for a motor configured to drive an operative device, e.g., a impeller, at a distal portion of the pump. It can be important for the motor to be configured to allow for percutaneous insertion of the pump's operative device.

SUMMARY

A problem associated with the positioning of prior art catheter pumps has been realized. Catheter pumps are disposed in a dynamic anatomical area in their normal use. That is, the pumping action of the heart includes movement of valve leaflets, heart walls, and blood vessels coupled with the heart. These movements and also the pressure waves associated with expulsion of blood from the left ventricle into the aorta are felt by the distal portion of the pump when it is positioned in the left ventricle. Percutaneously delivered catheter pumps are generally flexible to track through the arterial vasculature from a peripheral site. This flexibility makes the catheter pump more likely to be affected by these movement and pressure waves. It is important for direct unloading of the heart to keep the distal portion of the pump, which includes the blood intake, in the left ventricle. Shifting the intake out of the left ventricle (e.g. as a result of axial translation or dislocation) may result in pumping blood from the aorta which would have less benefit to the heart and could even deprive the coronary arteries of flow.

Also, more advanced, higher performance blood pumps have expandable impellers that may be housed in expandable blood flow conduits. Such devices rely on predictable stable gaps between the impeller tip and the inner wall of the blood flow conduit during operation. Prior art devices do not address these problems. There is a need therefore for techniques and/or structures to better enable high performance catheter pumps to maintain a proper position and to operate with high efficiency when disposed in the moving anatomy and subject to pressure fluctuations for extended periods of therapy.

In one embodiment, a catheter pump assembly is provided that includes an elongate body assembly, a shaft, and an impeller. The assembly has a proximal end, a distal end and at least one lumen extending therebetween. The shaft is disposed at least partially within the elongate body, e.g., in the at least one lumen, and is journaled for rotation. The impeller is coupled with a distal portion of the shaft. The impeller is configured to be rotated to induce flow of blood when the impeller is placed in fluid communication with a source of blood. An anchor can be disposed along an outer surface of the catheter pump at an intermediate location and configured to be deployed therefrom to engage a vascular segment to hold in place a portion of the catheter pump disposed in the patient. In some embodiments, the anchor can comprise an inflatable balloon brace disposed on an outer surface of the catheter pump. The inflatable balloon brace can be spaced proximally of the impeller and can have a low profile configuration for delivery through the vasculature and an expanded configuration for disposing (e.g., position and/or orienting) the impeller within the source of blood.

More generally, a device or structure is provided to retain the position of one or more parts of the catheter pump. The device or structure can be a brace that can be expandable, e.g., a stent-like frame that can be deployed from the catheter body. In some embodiments, the brace device can be one or a plurality of arms or struts that can be deployed from a side surface of a catheter body. Other brace devices can include coils or fins that can extend away from the catheter body to engage the vasculature.

In certain applications it is preferred to not disrupt or minimally affect the blood flow to locations downstream of the balloon brace. For this reason, in various embodiments one or more channels is provided around or through the balloon brace. The balloon brace can comprise a torus with an inflation member extending from the torus to the elongate body assembly. In one embodiment, the balloon brace comprises a spoke wheel that is expandable. The expansion of the wheel can be through an inflation lumen disposed in one or more of the spokes.

As an alternative to a balloon, the catheter body is placed in contact with the aorta as discussed above and a proximal portion of the catheter pump is affixed to another part of the patient. The proximal portion can be a portion of the catheter pump disposed outside the patient, e.g., at or adjacent to the percutaneous access site. The percutaneous access site is a femoral artery in one embodiment. The proximal fixation can thus be disposed at the leg, for example.

In one embodiment, a method is provided for positioning a catheter pump in a patient. In the method, a catheter pump is inserted into a peripheral vascular location. The catheter pump has an elongate body and a flow generating device disposed at a distal portion of the elongate body. The catheter pump has a brace disposed proximally of the flow generating device. The distal portion of the elongate body is advanced to a source of blood. The brace is deployed to reduce or minimize movement of at least a distal portion of the elongate body. The brace can include an extracorporeal securement device. The brace can include an expandable balloon brace.

In one method, the balloon brace is expanded from a side surface of the elongate body into contact with the vasculature. The contact preferably is close to the heart. In one embodiment, the contact with the vasculature is at a location from which a distal portion catheter pump can extend along a substantially straight path to the left ventricle. For example, the balloon brace can be deployed anywhere between the coronary arteries and the brachiocephalic artery. Placement at a location closer to the brachiocephalic artery than to the coronary arteries is advantageous in minimizing the chance of blocking the coronary arteries.

BRIEF DESCRIPTION OF THE DRAWINGS

A more complete appreciation of the subject matter of this application and the various advantages thereof can be realized by reference to the following detailed description, in which reference is made to the accompanying drawings in which:

FIG. 9 illustrates one embodiment of an impeller assembly;

FIGS. 9A, 9B-1, 9B-2, 10 and 10A illustrate details of further embodiments of impeller blades;

FIGS. 12, 12A, and 12B are cross-section views similar to that of FIG. 11, illustrating an infusate outflow path;

FIG. 14B is an enlarged view of a portion of another embodiment of the catheter assembly of FIG. 14 showing a mechanically deployable brace;

FIGS. 17A-D are perspective views of variations of a sheath assembly having an expandable distal portion;

More detailed descriptions of various embodiments of components for heart pumps useful to treat patients experiencing cardiac stress, including acute heart failure, are set forth below.

DETAILED DESCRIPTION

Major components of heart pumps that can be applied percutaneously to a patient are described below in Section I. Section II describes various structures that facilitate the rotatable support of a cantilevered impeller. Section III describes various structures that facilitate deployment and/or retrieval of one or more components of the distal end 108 of the heart pump 10 within the cardiovascular system.

Section IV describes various methods and techniques in connection with specific structures of heart pumps

I. Overview of Heart Pumps

Figure 1:
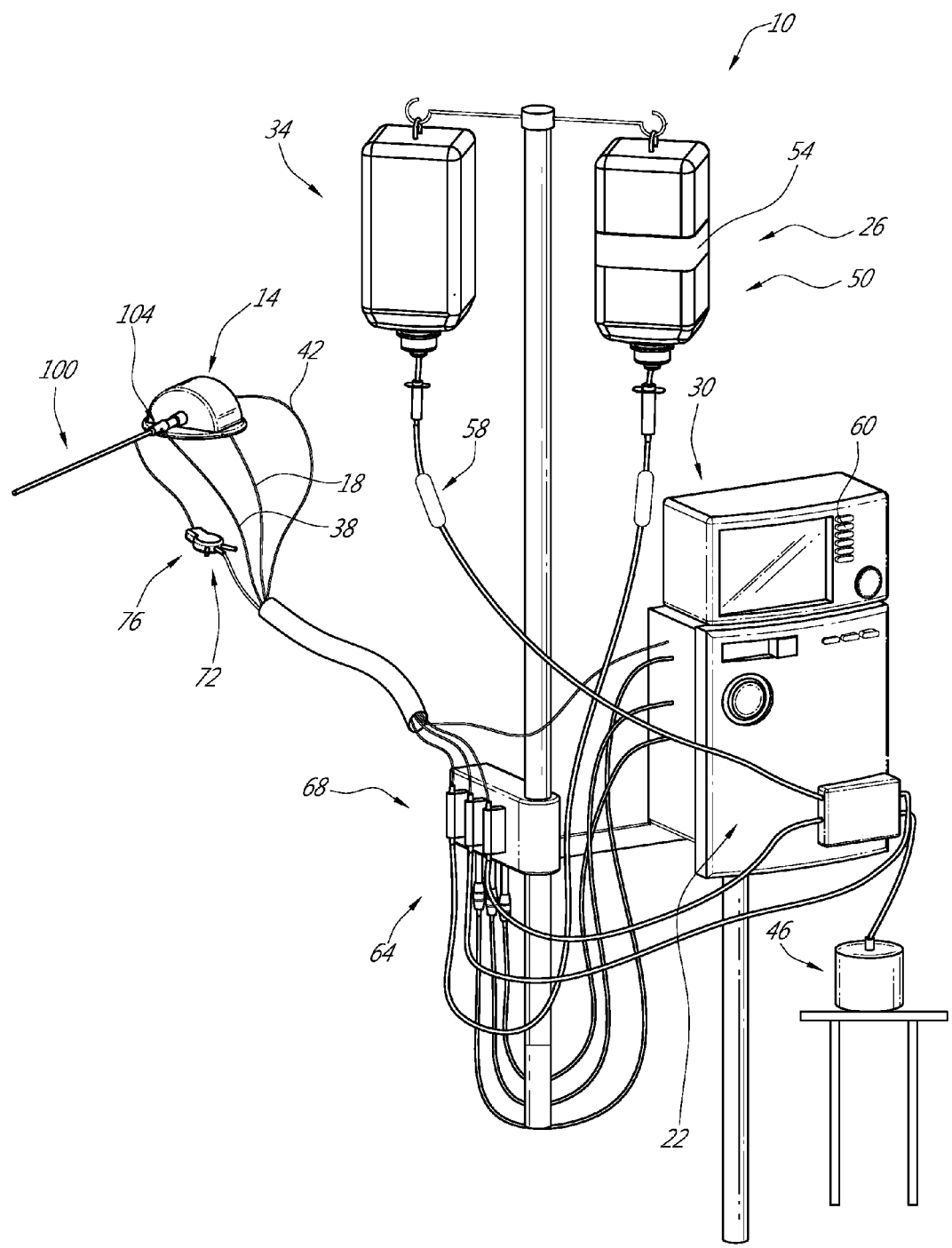
FIG. 1 illustrates one embodiment of a heart pump configured for percutaneous application and operation.

FIG. 1 illustrates one embodiment of a heart pump 10 that includes a catheter assembly 100 having a proximal end 104 adapted to connect to a motor 14 and a distal end 108 (see FIG. 1A) adapted to be inserted percutaneously into a patient. The motor 14 is connected by a signal line 18 to a control module 22 that provides power and/or control signals to the motor 14. As discussed further below, the heart pump 10 in various embodiments has an infusion or operating fluid system 26 and a patient monitoring system 30.

The infusion system 26 can provide a number of benefits to the heart pump 10 which are discussed below. In one embodiment, the infusion system 26 includes a source of infusate or operating fluid 34, a fluid conduit 38 extending from the infusate source 34 to the proximal end 104 of the catheter assembly 100 and a fluid conduit 42 extending from the proximal end of the catheter assembly 100 to a waste container 46. The flow of infusate to and from the catheter assembly 100 can be by any means, including a gravity system or one or more pumps. In the illustrated embodiment, the infusate source 34 includes an elevated container 50, which may be saline or another infusate as discussed below. Flow from the elevated container 50 can be regulated by a pressure cuff 54 to elevate the pressure of the fluid in the container 50 to increase flow or by a pinch valve 58 or by other means.

The patient monitoring system 30 can be used to monitor the patient and/or operation of the pump 10. For example, the patient monitoring system 30 can include a user interface 60 coupled with a source of data 64. The data source 64 can include one or more patient conditions sensors, such as pressure sensors 68 in pressure communication with the patient, and/or operating components within the patient. In one embodiment, the pressure sensors 68 fluidly communicate by a conduit 72 that extends between the sensors and a proximal portion of the catheter assembly 100. The conduit 72 can include a plurality of separable segments and can include a valve 76 to enable or disable the pressure communication to the sensors 68.

The heart pump 10 is adapted to provide an acute or other short-term treatment. A short-term treatment can be for less than a day or up to several days or weeks in some cases. With certain configurations the pump 10 can be used for a month or more.

The catheter assembly 100 extends between the proximal end 104 and the distal end 108. An impeller assembly 116 disposed at the distal end 108 is configured to pump blood to convey blood from one body cavity to another. In one arrangement, the impeller assembly 116 conveys blood proximally through or along a portion of the catheter assembly 100 to provide assistance to the left ventricle of the heart. In another embodiment, the impeller assembly 116 conveys blood distally through or along a portion of the catheter assembly 100 to provide assistance to the right ventricle of the heart. The heart pump 10 is useful as a heart assist device for treating patients with acute heart failure or other heart maladies. The heart pump 10 also can be used in connection with a surgical treatment to support the patient without providing full cardiovascular bypass. A patient could be supported on the device for longer term with proper controls and design.

The catheter assembly 100 is provided with a low profile configuration for percutaneous insertion. For example, the distal end 108 of the catheter assembly 100 can be configured to have about an 11 French (approximately 3.5 mm) size in a first configuration for insertion and an expanded configuration, such as up to about 21 French (approximately 7 mm), once positioned in the body. The larger size facilitates greater flow rates by the impeller assembly 116 as discussed below.

The catheter assembly 100 is configured to enable the distal end 108 to reach a heart chamber after being inserted initially into a peripheral vessel. For example, the catheter assembly 100 can have a suitable length to reach the left ventricle and sufficient pushability and torquability to traverse the intervening vasculature. The catheter assembly 100 may include a multilumen catheter body 120 that is arranged to facilitate delivery and operation of the impeller assembly 116. Variations of the catheter body 120 also can include inflation lumens for deploying a brace as discussed below in Section III(A). Further details concerning various embodiments of the catheter body 120 are discussed below in connection with FIGS. 7-7C.

A drive system is provided to drive an impeller within the impeller assembly 116. The drive system includes a motor 14 and a suitably configured drive controller disposed within the control module 22. The motor 14 in various embodiments is configured to be disposed outside the patient, e.g., adjacent to the proximal end 104 of the catheter assembly 100. In one advantageous embodiment, the drive system employs a magnetic drive arrangement. The motor 14 is arranged to generate magnetic fields that will be sensed by permanent magnets disposed within the proximal end 104 of the catheter assembly 100. This arrangement facilitates very efficient generation of torque used to drive the impeller assembly 116, as discussed below.

Some embodiments described herein could be incorporated into a system in which a motor is miniaturized sufficiently to be inserted into the patient in use, including into the vasculature. Such an embodiment could be operated by disposing control signal lines within the proximal portion of the catheter body 120. Also, it may be useful to provide the capability to measure blood pressure at the distal end 108 using a device disposed at the proximal end 104. For example, a pressure sensor at the distal end can communicate with a device outside the patient through a lumen of the catheter body 120. Various details of these optional features are described in U.S. Pat. No. 7,070,555, which is incorporated by reference herein for all purposes and in its entirety.

In another embodiment, a mechanical interface can be provided between the motor and the proximal end 104 of the catheter assembly 100. The mechanical interface can be between the motor 14 and a drive shaft positioned at the proximal end of the catheter assembly 100.

Figure 11:
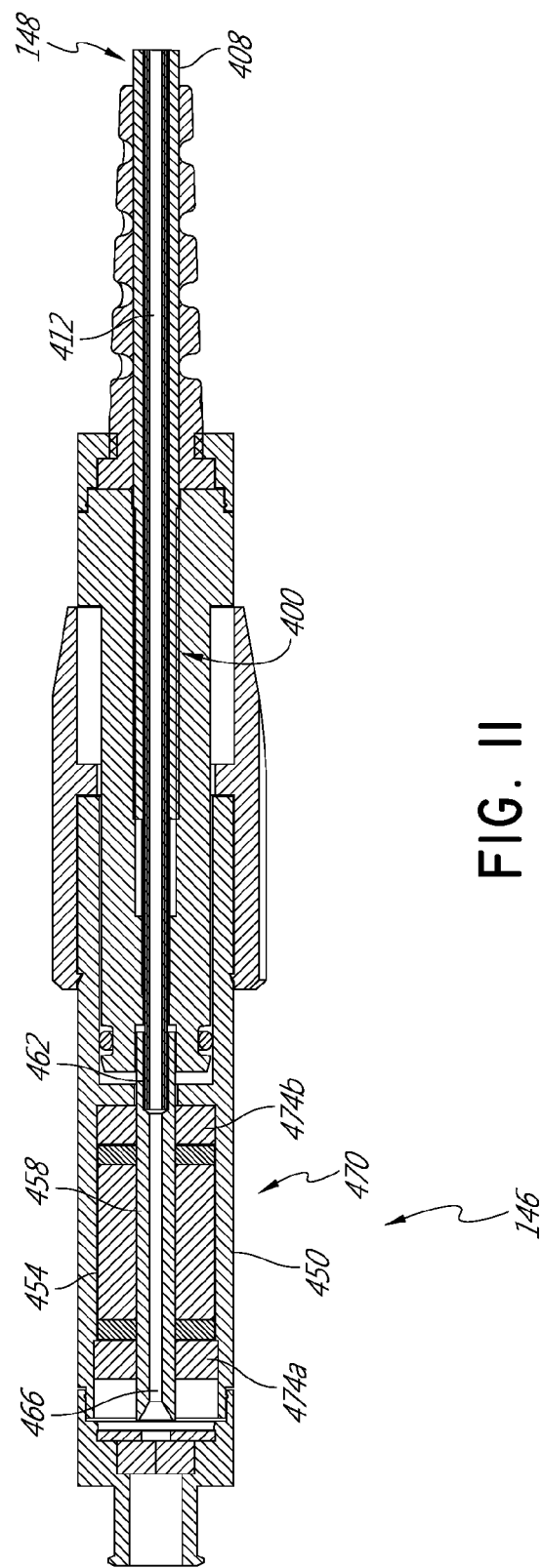
FIG. 11 is a cross-sectional view of a proximal portion of the catheter assembly, taken through the section plane 11-11 on FIG. 1A.

A torque coupling system is provided for transferring torque generated by the drive system to the impeller assembly 116. The torque coupling system is discussed further in Section II(C)—Torque Coupling System (as discussed below), but in general can include magnetic interface between the motor 14 and a driven assembly 146 disposed at the proximal end 104 of the catheter assembly 100. The driven assembly 146 is coupled with a proximal end of an elongate drive shaft 148 in one embodiment. The drive shaft 148 extends between the driven assembly 146 and the impeller assembly 116. A distal portion of the drive shaft 148 is coupled with the impeller assembly 116 as discussed below in connection with one embodiment illustrated in FIGS. 4A and 4B. FIG. 11 shows one manner of coupling the proximal end of the drive shaft 148 with the driven assembly 146.

Figure 1A:
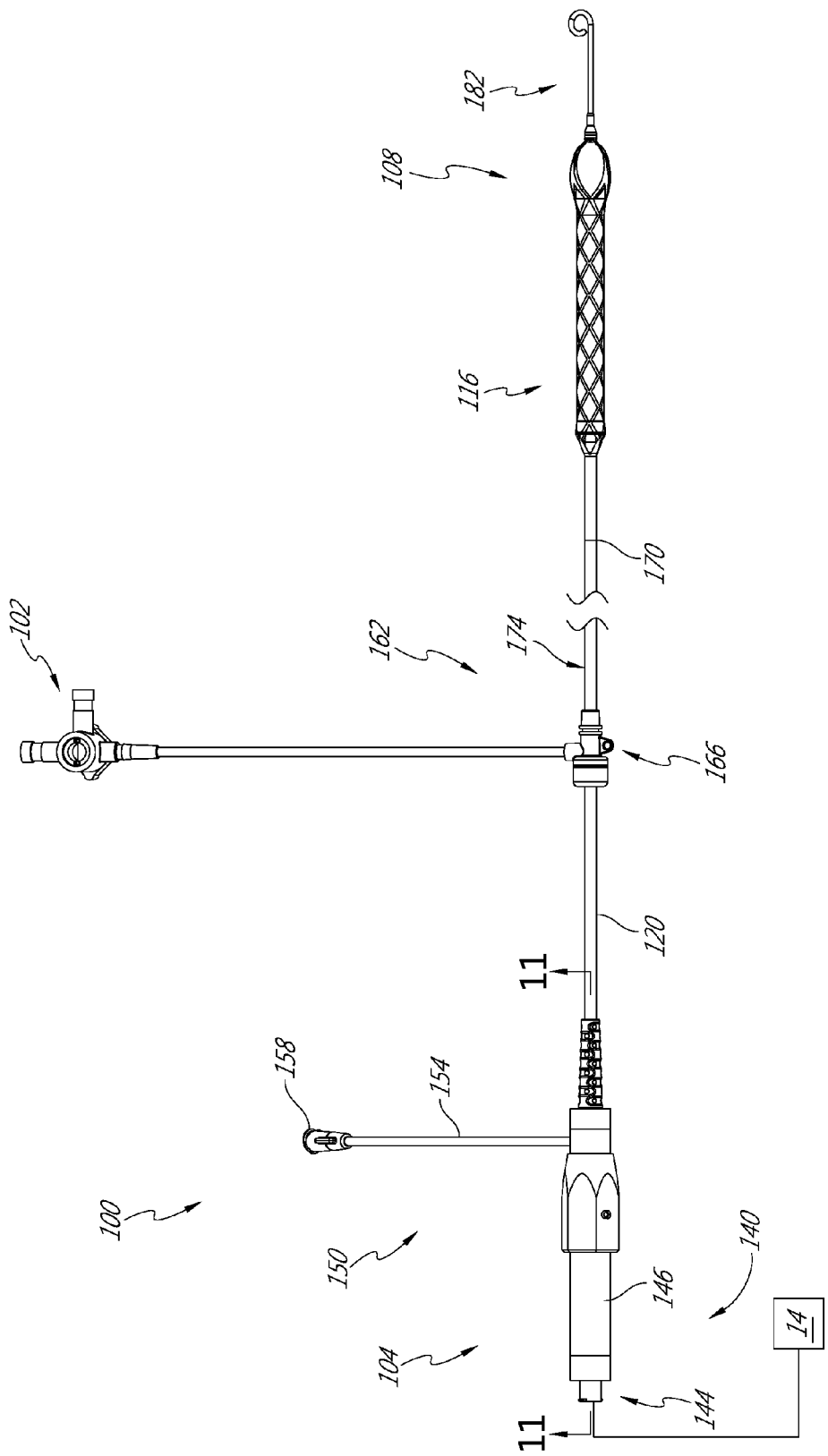
FIG. 1A is a plan view of one embodiment of a catheter assembly adapted to be used with the heart pump of FIG. 1.

As discussed above, the heart pump 10 may also include an infusion system 26. FIG. 1A shows that the infusion system 26 can include an infusion inflow assembly 150 provided adjacent to the proximal end 104 in one embodiment. The infusion assembly 150 can be one component of an infusion system that is configured to convey one or more fluids within the catheter assembly 100. The fluids can be conveyed distally within the catheter assembly 100, e.g., within the catheter body 120, to facilitate operation of the impeller assembly 116, some aspect of a treatment, or both. In one embodiment, the infusion system is configured to convey a lubricant, which can be saline, glucose, lactated Ringer's solution, acetated Ringer's solution, Hartmann's solution (e.g., including compound sodium lactate), and D5W dextrose solution. In another embodiment, the infusion system is configured to convey a medication, or a substance that both acts as lubricant and medication. As sometimes used herein "infusate" is intended to be a broad term that includes any fluid or other matter that provides performance enhancement of a component of the heart pump 10 or therapeutic benefit, and can be wholly or partly extracted from the system during or after operation of the pump. The infusate is one example of an operating fluid.

In one embodiment, the infusion inflow assembly 150 includes a catheter body 154 having a luer or other suitable connector 158 disposed at a proximal end thereof and an inflow port in fluid communication with one or more lumens within the catheter assembly 100. A lumen extending through the catheter body 154 is adapted to be fluidly coupled with a fluid source connected to the connector 158 to deliver the fluid into the catheter assembly 100 and through one or more flow paths as discussed below in connection with FIGS. 4A, 4B, and 7-7C.

FIGS. 1A and 12 show that the catheter assembly 100 in various embodiments also includes an outlet positioned at a location that is outside the patient when the heart pump 10 is in use to allow infusate to be removed from the pump and from the patient during or after the treatment. The outlet can be fluidly coupled with an infusate return flow path in the catheter body 120 through a fluid port 144 disposed at the proximal end 104.

The catheter assembly 100 can also include a sheath assembly 162 configured to constrain the impeller assembly 116 in a low profile configuration in a first state and to permit the impeller assembly 116 to expand to the enlarged configuration in a second state. The sheath assembly 162 has a proximal end 166, a distal end 170, and an elongate body 174 extending therebetween. In one embodiment, the elongate body 174 has a lumen extending between the proximal and distal ends 166, 170, the lumen being configured to be slidably disposed over the catheter body 120. The arrangement permits the sheath assembly 162 to be actuated between an advanced position and a retracted position. The retracted position is one example of a second state enabling the impeller assembly 116 to expand to an enlarged configuration. As discussed further below in Section III(A), a retracted position also can expose a brace or support device to be actuated during placement of a portion of a catheter pump assembly. The advanced position is one example of a first state that enables the impeller assembly 116 to be collapsed to the low profile configuration. In some embodiments, a luer 102 or other suitable connector is in fluid communication with the proximal end 166 of the sheath assembly 162. The luer 102 can be configured to deliver fluids to the catheter assembly 100, such as priming fluid, infusate, or any other suitable fluid.

FIG. 1A illustrates a retracted position, in which the distal end 170 of the elongate body 174 is at a position proximal of the impeller assembly 116. In an advanced position, the distal end 170 of the elongate body 174 is positioned distal of at least a portion of the impeller assembly 116. The sheath assembly 162 can be configured such that distal advancement of the distal end 170 over the impeller assembly 116 actuates the impeller assembly 116 from an enlarged state to a more compact state (or low profile configuration), e.g., causing a change from the second state to the first state, as discussed above.

Figure 4A:
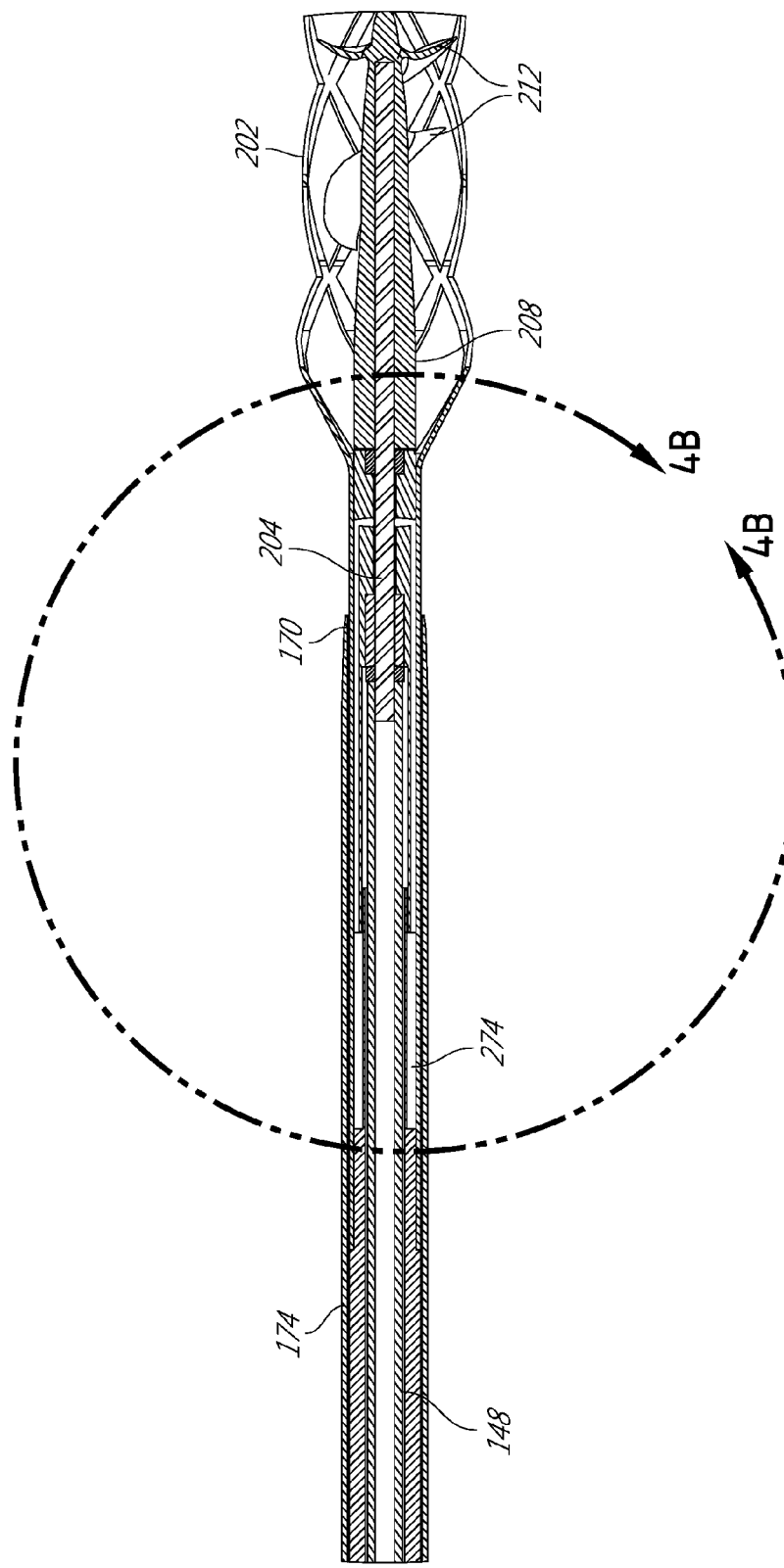
FIG. 4A is a cross-sectional view of a distal portion of the catheter assembly, taken through the section plane 4A-4A shown in FIG. 2.
Figure 4B:
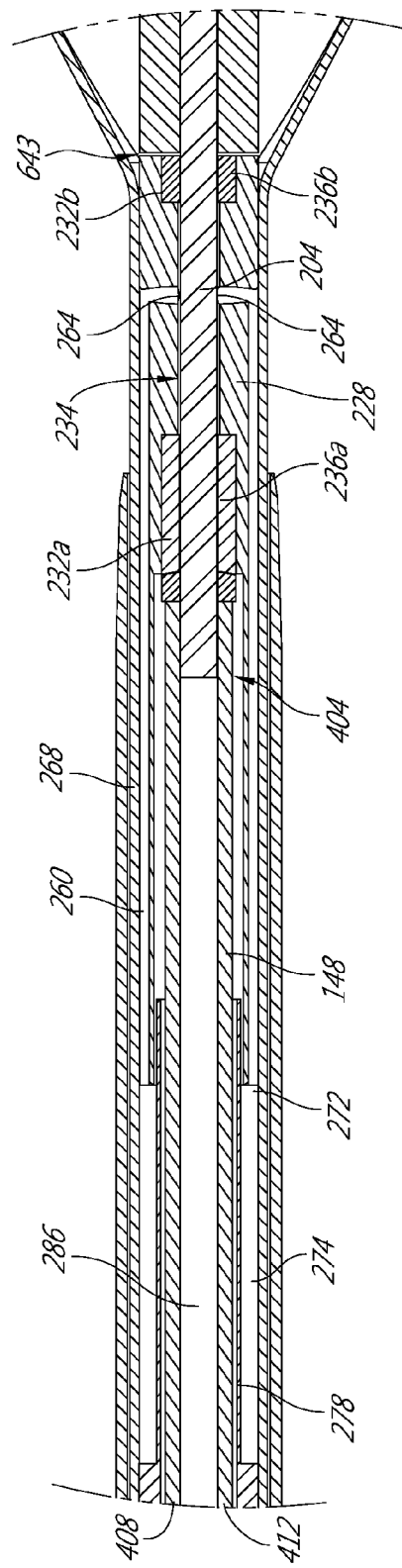
FIG. 4B is a detail view of the distal portion of the catheter assembly, taken at 4B-4B shown in FIG. 4A.

FIGS. 4A & 4B show the elongate body 174 as a single layer structure from the inner surface to the outer surface thereof. In another embodiment, the elongate body 174 has a multilayer construction. In one arrangement, the elongate body 174 has a first layer that is exposed to the catheter body 120 and a second layer exposed that corresponds to an outer surface of the catheter assembly 100. A third layer can be disposed between the first and second layers to reinforce the elongate body 174, particularly adjacent to the distal end thereof to facilitate collapse of the impeller assembly 116. In another construction, a reinforcing structure can be embedded in an otherwise continuous tubular structure forming the elongate body 174. For example, in some embodiments, the elongate body 174 can be reinforced with a metallic coil.

Figure 2:
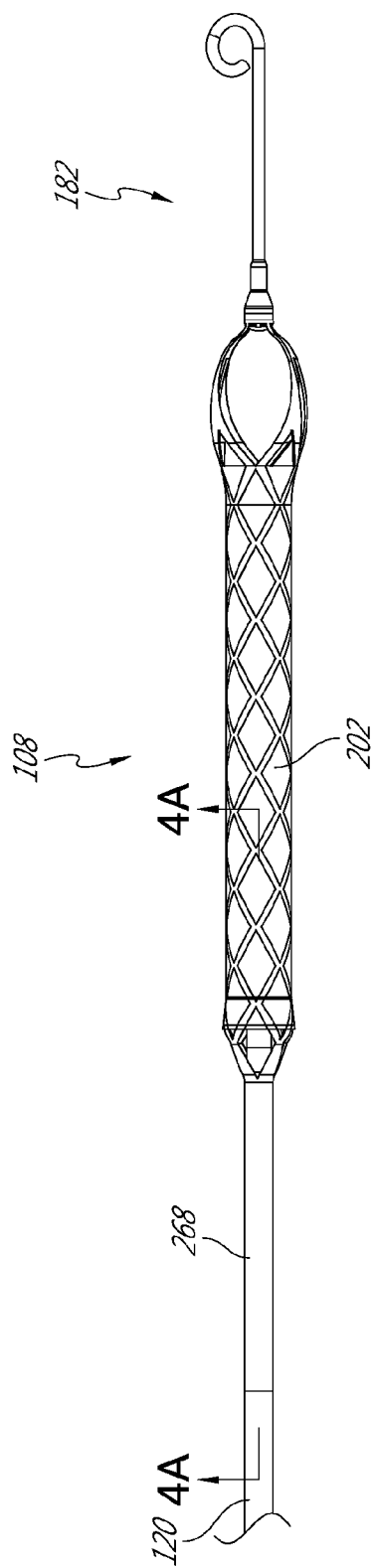
FIG. 2 is a detail view of a distal portion of the catheter assembly illustrated in FIG. 1A.

FIG. 2 show that an impeller housing 202 is disposed at the distal end 108. The impeller housing 202 can be considered part of the impeller assembly 116 in that it houses an impeller and provides clearance between the impeller and the anatomy to prevent any harmful interactions therebetween. The housing 202 and the impeller are also carefully integrated to maintain an appropriate flow regime, e.g., from distal to proximal or from proximal to distal within the housing.

FIGS. 1A and 2 also show that the distal end 108 of the catheter assembly 100 includes an atraumatic tip 182 disposed distal of the impeller assembly 116 in one embodiment. FIG. 1A shows that the atraumatic tip 182 can have an arcuate configuration such that interactions with the vasculature are minimally traumatic. The tip 182 can also be configured as a positioning member. In particular, the tip 182 can be rigid enough to help in positioning the impeller assembly 116 relative to the anatomy. In one embodiment, the tip 182 is rigid enough that when it is urged against a heart structure such as the ventricle wall, a tactile feedback is provided to the clinician indicating that the impeller assembly 182 is properly positioned against the heart structure.

II. Impeller Rotation and Support

The impeller assembly 116 can take any suitable form, but in various embodiments includes an impeller 200 adapted to move a fluid such as blood from an inlet to an outlet of the catheter assembly 100. In certain embodiments the impeller 200 can be cantilevered or otherwise supported for rotation primarily at one end.

Figure 3:
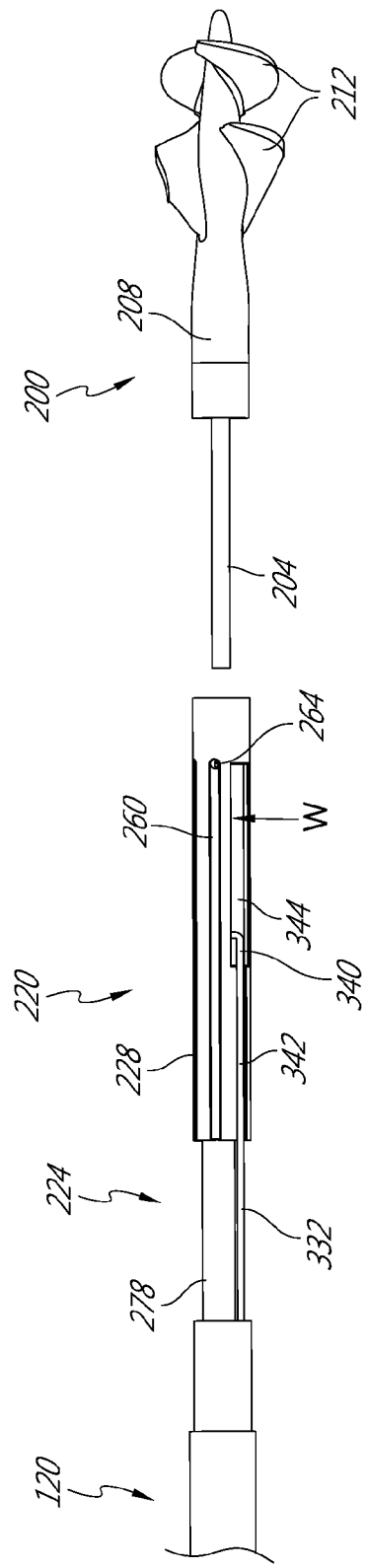
FIG. 3 is an exploded view of a portion of an impeller assembly of the catheter assembly of FIG. 1A.

FIG. 3 shows that the impeller 200 includes a shaft 204, a central body or hub 208, and one or more blades 212.

Figures 1, 9B:
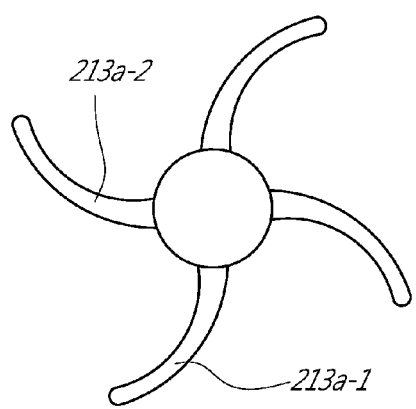
Figures 2, 9B:
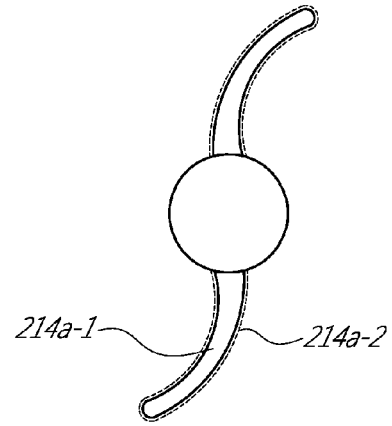
Figure 10:
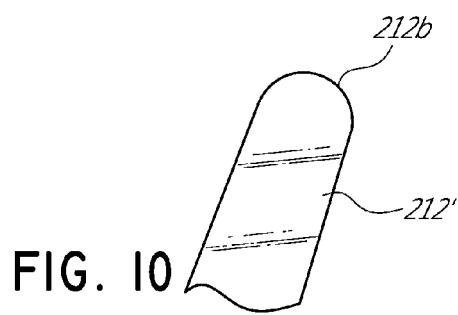
Figure 10A:
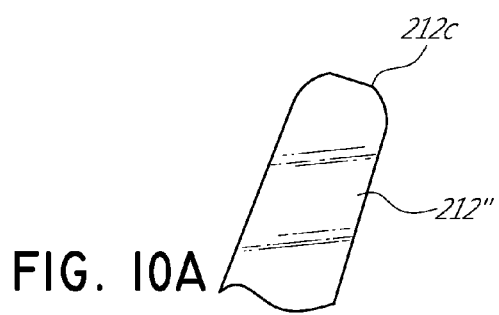

The shaft 204 and hub 208 can be joined in any suitable fashion, such as by embedding a distal portion of the shaft within the hub 208. The blades 212 can be spaced out proximal to distal along the axis of the shaft. In some embodiments, the blades 212 are provided in blade rows. FIG. 9 shows that the distal end of the shaft 204 can extend at least to an axial position corresponding to one of the blade rows. In some embodiments, the shaft 204 can be solid. In other embodiments, the shaft 204 has a lumen extending axially through the hub so that a guidewire can be passed through the catheter assembly 100. Details of variations with a lumen are discussed further in U.S. Application Publication No. 2011/0004046A1, Published Jan. 6, 2011, titled Blood Pump With Expandable Cannula, which is hereby incorporated by reference herein in its entirety and for all purposes. Additional details of the impeller may be found throughout U.S. Pat. No. 8,721,517, issued May 13, 2014, which is incorporated by reference herein in its entirety and for all purposes.

A. Operating Fluid Delivery and Removal System

The operation and duty cycle of the impeller assembly 116 can be lengthened by providing a hydrodynamic bearing for supporting the shaft 204. A hydrodynamic bearing can be supported by an operating fluid such as isotonic saline or other lubricant, which can be delivered in a continuous flow. The lubricant can be delivered through the infusion system to an outside surface of the shaft 204. The infusate may be directed onto the shaft from a radially outward location. In some arrangements, the lubricant flow is controlled such that of a total lubricant volume introduced into the proximal end of the cannula, a first portion of the total volume of the lubricant flows proximally along the shaft 204. In some embodiments, a second portion of the total volume flows distally along the shaft, the first volume being different from the second volume. The second portion of the total volume can be substantially equal to the total volume introduced into the proximal end of the cannula less the first volume.

FIGS. 3 to 8 show various structures for providing rotational support of a proximal portion of the shaft 204 within the distal portion of the catheter assembly 100. For example, as shown in FIG. 3, a bearing assembly 220 can be disposed at a distal end 224 of the multilumen catheter body 120. In one embodiment, the bearing assembly 224 includes a housing 228 (as shown in FIG. 4B) and one or more bearings configured to support the proximal portion of the shaft 204. The bearing assembly 224, as illustrated in more detail in FIG. 4B, includes a plurality of bearings 232a, 232b disposed within the bearing housing 228. Various materials that can be used for the bearings are discussed below.

Figure 6:
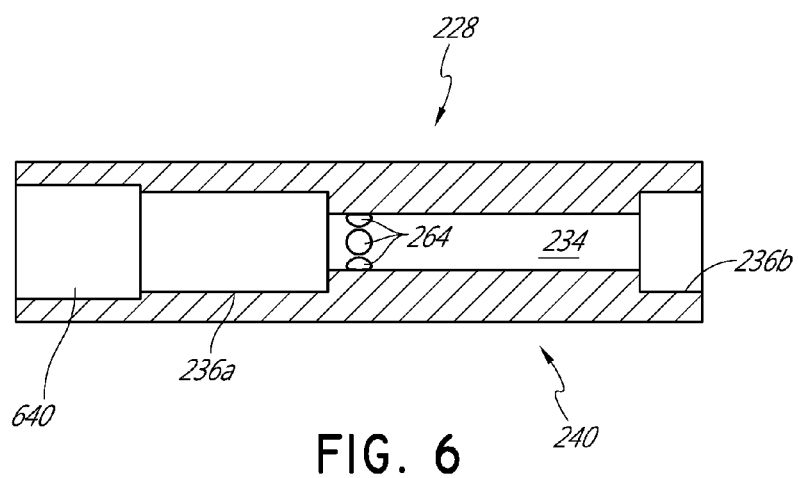
FIG. 6 is a cross-sectional view of a bearing housing of the bearing assembly of FIG. 5.

FIG. 6 shows that the bearing housing 228 has a lumen 234 extending therethrough with a proximal enlarged portion 236a and a distal enlarged portion 236b. The housing 228 comprises a shoulder defining a narrow portion 240 of the lumen 234 disposed between the enlarged portions 236a, 236b. The first and second bearings 232a, 232b can be disposed within the enlarged portions 236a, 236b of the bearing housing 228.

In one arrangement, the proximal end of the shaft 204 (e.g., as shown in FIG. 4A) is received in and extends proximally of the second bearing 232b. In some embodiments there can be one bearing (e.g., only bearing 232a), while in other embodiments both bearings 232a and 232b can be used. In some embodiments, the bearing(s), e.g., bearings 232a and/or 232b, can be friction fit or interference fit onto the impeller shaft 204. Accordingly, the shaft 204 can be supported for rotation by the bearings 232a, 232b as well as in the narrow portion 240 of the housing 228. In embodiments where the bearing(s) 232a, 232b are friction or interference fit onto the shaft, the bearing(s) 232a, 232b can be configured to rotate with the shaft 204 relative to the bearing housing 228. Further, the bearing(s) 232a, 232b can have a relatively large clearance with the bearing housing 228. The clearance between the shaft 204 and the bearing housing 228, at regions that are not coupled with the bearing, can be in the range of about 0.0005 to about 0.001 inch. In certain embodiments, the clearance can be within a larger range, such as at least about 0.0005 inches, about 0.001 inches or up to about 0.005 inches. In embodiments with multiple bearing(s) 232a, 232b, the clearance can be different for the bearings 232a, 232b, such as providing a larger clearance at the proximal bearing 232a.

Figure 5:
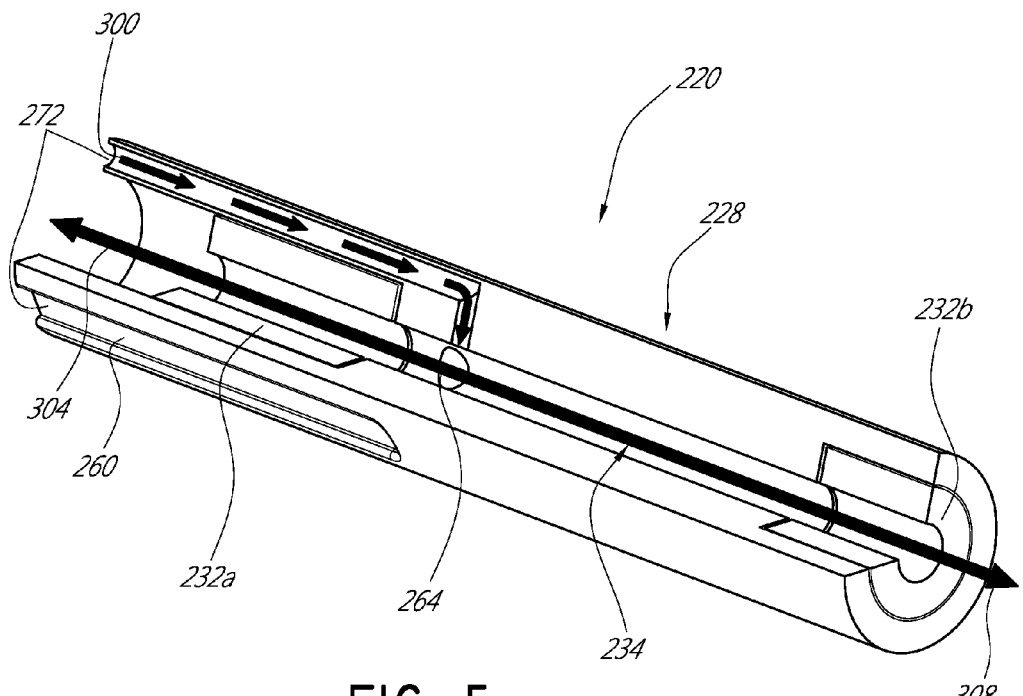
FIG. 5 is a cross-sectional perspective view of a bearing assembly of the catheter assembly of FIG. 1A.

In other embodiments, such as in FIG. 5, the bearing(s) 232a, 232b may not be friction or interference fit onto the shaft 204. In these embodiments, the bearing(s) 232a, 232b may be disposed within the bearing housing 228, for example by an interference or press fit. The shaft 204 may then rotate with respect to the bearing(s) 232a, 232b, and there can be a clearance between the shaft 204 and the bearing(s) 232a, 232b. The clearance between the shaft 204 and the bearings 232a, 232b can be in the range of about 0.0005 to about 0.001 inch. In certain embodiments, the clearance can be within a larger range, such as at least about 0.0005 inches, about 0.001 inches or up to about 0.005 inches. The clearance can be different for the bearings 232a, 232b, such as providing a larger clearance at the proximal bearing 232a. In certain embodiments, the bearing housing 228 may provide a thrust surface for bearing axial loads. In other embodiments, there may be other bearings located either distally or proximally of the bearing housing 228 that are configured to bear axial loads. In other embodiments, the fit between the bearings 232a, 232b and the shaft 204 can be tight, which can also assist in bearing axial loads in some aspects.

At least the proximal portion of the shaft 204 can be made of a material that will not corrode or otherwise be made to be inert when immersed in the lubricant or other infusate. The material may be one that will not corrode in isotonic saline. Suitable materials may include a wide variety of metals, including alloys, and at least saline-resistant stainless steel and nickel-based alloys. Also, the shaft 204 could be made as a composite to include advantageous properties of a plurality of materials. In some cases the shaft 204 could be formed as a polymer. The class of polymers selected would include those that can form a shaft 204 of a certain stiffness suitable in this application. For example, polycarbonate or PEEK could be used. In certain configurations, the polycarbonate, PEEK, or other suitable polymer can provide enhanced performance by being combined with a second material or structure. A glass or carbon filled polycarbonate or other stiff polymer could also be used.

As discussed above, a hydrodynamic bearing between the shaft 204 and the bearings 232a, 232b may be utilized in various embodiments. In one such arrangement, a continuously replenished fluid film is provided at least between the inner wall of the bearing housing and an adjacent moving structure, such as the impeller shaft or an outer surface of a bearing. For example, the bearing housing 228 can be configured to permit a lubricant to be delivered therethrough into the lumen 234. The bearing housing 232 can include a plurality of channels 260 disposed therein extending proximally from a plurality of ports 264 located at the narrow portion 240 of the housing 228. Each port 264 can communicate with one of the channels 260 to provide fluid communication into the lumen 234.

As shown in FIG. 5, the channels 260 can be formed in the wall of the housing 228. In one embodiment, the channels 260 are formed as open depressions, e.g., as flutes, extending along the housing 228. In this embodiment, the channels 260 can be enclosed by a separate structure, such as a separate outer sleeve, that is disposed around the housing 228. FIG. 4B shows that a proximal portion 268 of the impeller housing 202 can be sized to tightly fit over the outer surface of the bearing housing 228, enclosing the radially outward portion of the channels 260. In this arrangement, at least a portion of a flow path is formed between an outer surface of the bearing housing 232 and a separate outer sleeve.

Fluid communication between the port 264 in the bearing housing 228 and the infusion inflow assembly 150 can be by any suitable combination of lumens within the catheter assembly 100. For example, in one embodiment, each of the channels 260 has a proximal port 272 that communications with an annular space 274 formed in the catheter assembly 100. The annular space 274 can be formed between a plurality of separate overlaid structures in the catheter assembly 100. FIGS. 4A and 4B show that the annular space 274 is formed between an outer surface 278 of the multilumen catheter body 120 and an inner surface of the proximal length 268 of the housing 202.

Figure 7:
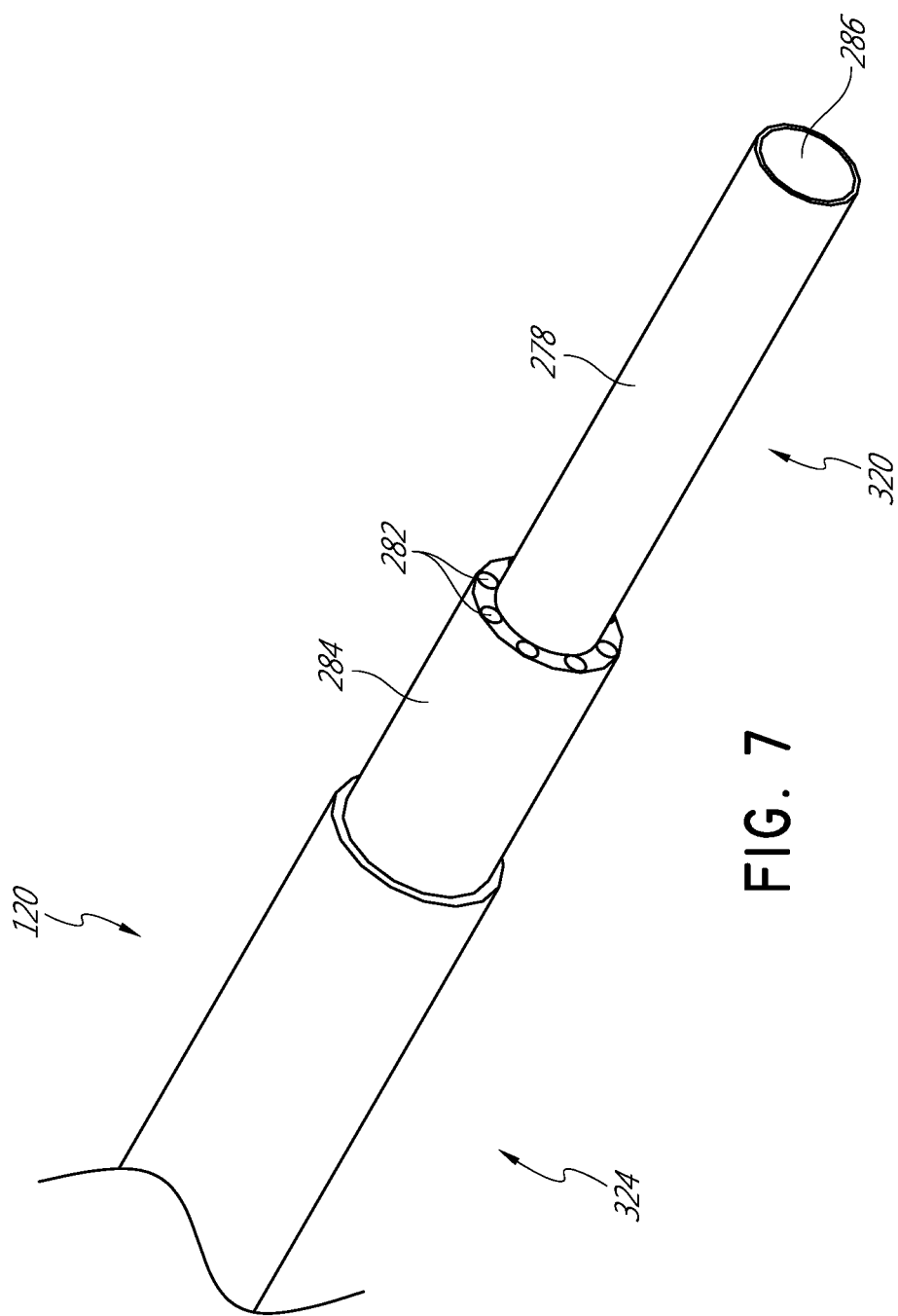
FIG. 7 is a perspective view of one embodiment of a catheter body that can be used to house a drive shaft and to convey an infusate to the bearing housing of FIG. 5.
Figure 7C:
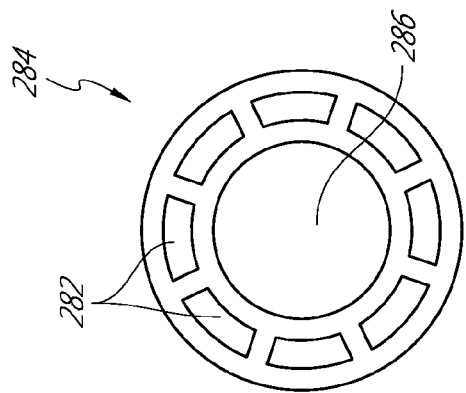
FIGS. 7A-7C show variations of the catheter body of FIG. 7.
Figure 7B:
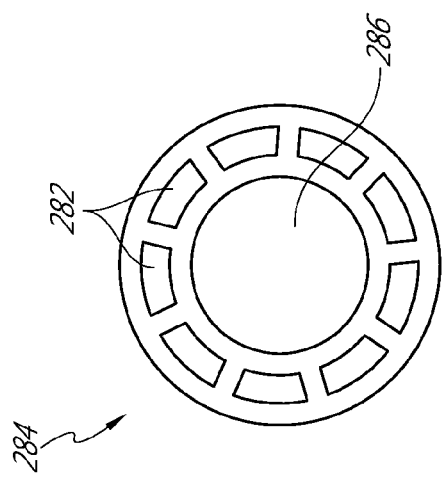
Figure 7A:
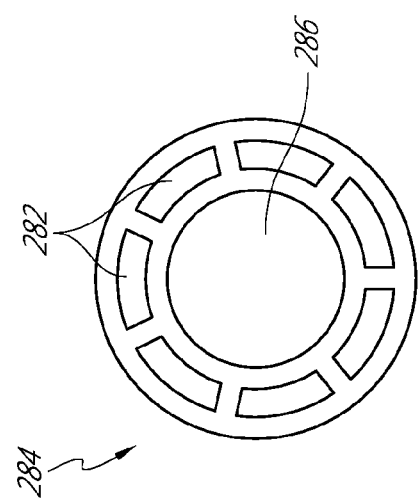

Fluid communication is provided in the catheter assembly 100 between the space 274 and the infusion inflow assembly 150. For example, a plurality of lumens 282 formed in the multi-lumen catheter body 120 can be dispersed circumferentially about the catheter body 120 at a peripheral circumferential region 284, as illustrated in FIGS. 7-7C. The peripheral position of the lumens 282 enables a central area of the catheter body 120 to be dedicated to a central lumen 286. By providing a plurality of smaller lumens 282 located at the periphery, a relatively large flow rate can be delivered through a relatively small circumferential band (when considered in cross-section) of the catheter body 120. In some embodiments, each of the lumens 282 has a distal port 290 that communicates with the space 274. In some embodiments, one or more of the lumens 282 can be in fluid communication with an inflatable balloon brace as discussed further below in connection with FIGS. 15-16C.

A proximal portion of the lumens 282 can take any suitable form. For example, the lumens 282 can communicate at their proximal end with a flow diverting structure (not shown) that is in fluid communication with the infusion inflow assembly 150. As described herein, in some embodiments the lumen 282 can be disposed circumferentially about the central lumen 286. The catheter assembly 100 can include a flow diverting structure or connector, e.g., disposed about the proximal end of the catheter body 120 that is configured to divert the infusate into the lumens 282 for distally directed flow therein. In other embodiments, the catheter assembly 120 can include a flow diverting structure disposed adjacent the distal end thereof that is configured to divert the infusate into the lumens 282 from the central lumen 286 for proximally directed flow in the lumens 282.

FIG. 5 includes arrows that illustrate the flow of infusate into the bearing assembly 220. In one arrangement, the inflow of infusate is indicated by an arrow 300 which is shown pointing distally within one of the channels 260 of the bearing housing 228. The infusate flow enters the bearing housing through the ports 264. Although flow is shown in one channel 260, corresponding flow may be provided in each of a plurality of channels 260 disposed around the central lumen 234. An arrow 304 illustrates that at least a portion of the infusate delivered through the port 264 may flow generally proximally within the bearing housing 228. An arrow 308 illustrates that at least a portion of the infusate delivered through the port 264 may flow generally distally within the bearing housing 228.

FIG. 5 illustrates the arrows 304, 308 as proximally and distally directed, respectively. However, the high speed rotation of the impeller shaft 204 within the housing 228 will create a thin film of lubricant spacing the impeller shaft 204 from the surfaces of the bearings 232a, 232b. This thin film will extend all the way around the shaft 204 and thus each portion of the flow will have a spiral or helical flow direction.

The bearings 232a, 232b can have different configurations to enhance the performance of the pump 10. For example, the proximal bearing 232a can be longer along the longitudinal axis of the bearing housing 228 than the distal bearing 232b. A longer proximal bearing 232a is believed to better control runout of the shaft 204. Better runout control on the shaft 204 is believed to enhance the control of the position of the blades 212 relative to the housing 202. Less runout reduces excessive variation in the gap between the blades 212 and the housing 202, providing biocompatibility benefits such as reduced hemolysis.

In some embodiments, such as those in FIG. 5 where the bearings 232a, 232b are not friction fit or interference fit onto the shaft 204, the distal bearing 232b has a smaller inner diameter than the proximal bearing 232a. If the shaft 204 has a constant diameter, the smaller inner diameter should provide greater control of angular deflection of the shaft. Controlling angular deflection can enhance relative position control of the blades 212 and housing 202, providing blood handling benefits such as reduced hemolysis. A smaller clearance could also be provided by enlarging the diameter of the shaft 204 at the axial position of the distal bearing. In some embodiments, the larger inner diameter of the bearing 232b enables a larger volume of lubricant to flow proximally and a lesser volume to flow distally in the lumen 234.

The continuous introduction of lubricant maintains a constant, predictable and durable rotational bearing state between stationary component, e.g., the bearing housing 282, and a moving component, e.g., the shaft 204, a component of the bearings 232a, 232b, or both the shaft 204 and a component of the bearings 232a, 232b. Also, continuous lubricant inflow provides a means for removing heat generated by the relative motion between the shaft 204 and the bearings. Also, the infusate can create fluid pressure within the catheter assembly 100 that can push debris generated within or by the pump 10 out of the bearing housing 220. Enhancing the volume of infusate that flows along the path indicated by the arrow 304 enhances the likelihood that debris generated by or present in the pump will be removed from the proximal end rather than to be trapped inside the distal portion of the catheter assembly 100.

Another technique for controlling infusate flow in the lumen 234 is to locate the port 264 between the bearings 232a, 232b and closer to one of the bearing. For example, the ports 264 can be located adjacent to the proximal bearing 232a in one embodiment. This provides a shorter path of egress out of the narrow portion 240 of the bearing housing 228 in the proximal direction.

Figure 8:
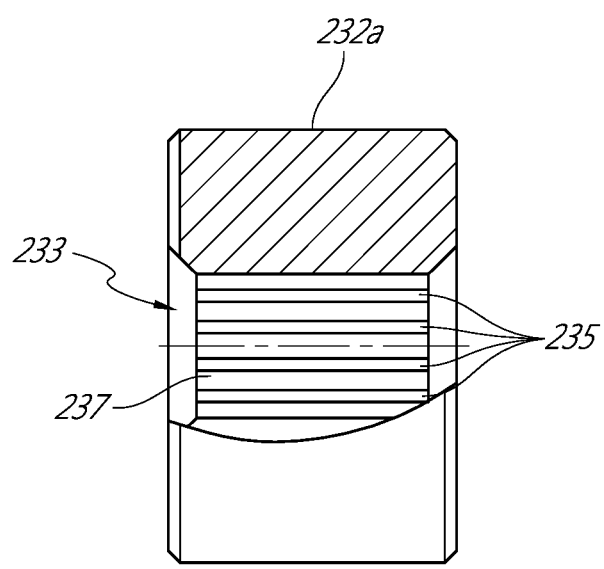
FIG. 8 illustrates a surface configuration of one embodiment of a bearing adapted to enhance or control flow of an infusate in the bearing assembly of FIG. 5.

Other strategies for controlling the flow of infusate within the bearing housing 228 include modifying a surface within one or more of the bearings 232a, 232b. FIG. 8 shows a surface modification 233 provided in a bearing 232a to enhance proximally directed flow. The surface modification 233 comprises a plurality of axially oriented grooves 235 in one embodiment. In another embodiment, the surface modification 233 includes one or more spiral grooves. The spiral grooves can be formed with a groove entrance that is substantially parallel with a flow direction of infusate between the bearings 232a, 232b such that a reduction of velocity of the flow is minimized. In one embodiment, each spiral groove includes at least about 3 turns disposed on the inner surface of the bearing between the proximal and distal ends of the bearing. In another embodiment, each spiral groove has adjacent turns that are spaced apart by a minimum pitch of 0.125 inches (3.2 mm). In another embodiment, each spiral groove has an axial density of about 32 turns per inch (about 1.3 turns per mm). The grooves are formed in the surface 237 of the bearing 232a upon which the impeller shaft 204 is supported. The grooves 235 locally enlarge the clearance between the shaft 204 and the surface 237 so that a greater volume of infusate can flow distal-to-proximal across the bearing 232a. The surface modification 233 reduces back-pressure limiting the distal-to-proximal flow across the bearing 232a.

In other embodiments, it may be desirable to enhance distally directed flow. For example, the infusate may be provided with a fluid intended to be delivered to the patient. In such embodiments, the surface modification 233 can be provided on the distal bearing 232b. In certain embodiments, both proximal and distal bearings 232a, 232b are provided with flow enhancing modifications to enhance heat transfer or purging of the bearing assembly 220. In such embodiments, one of the bearings may have a greater degree of flow enhancement provided on the bearing surface.

The arrangement of the bearing assembly 220 can be a factor in selecting an appropriate infusate. Saline is a preferred infusate, but other sufficiently biocompatible infusates could be used. Other embodiments are configured such that little or no infusate flows out of the pump into the patient. For such embodiments, other infusate fluids can be used, such as glucose.

FIG. 7 illustrates further features of the catheter body 120. The catheter body 120 comprises an inner most portion 320 that defines the central lumen 286. The inner most portion 320 is disposed within, e.g., circumferentially surrounded by, the peripheral circumferential region 284. A continuous outer circumferential region 324 can be provided around the peripheral circumferential region 284 to fully enclose the lumens 282, discussed above. FIGS. 4A and 4B illustrate that a distal end of the inner most portion 320 is configured to be received and secured within a proximal portion of the lumen 234 within the bearing housing 228. FIG. 4B illustrates that a region of overlap can be provided between a distal portion of the inner most portion 320 and a proximal portion of the bearing housing 228. This construction provides a continuous lumen defined in part by the central lumen 286 of the catheter body 120 and in part by the lumen 234 of the bearing housing. In another arrangement, the bearing housing 228 and the catheter body 120 are joined by a coupler that enhances the sealing between infusate inflow through the lumens 282 and the channels 260 and the infusate outflow through the central lumen 286. As discussed further below, this continuous lumen provides a space for the rotation of the shaft 204 of the impeller assembly 116 and the drive shaft 148 of the torque coupling system.

The physical connection between the bearing housing 228 and the catheter body 120 can be achieved in any suitable manner. FIG. 3 illustrates that in one arrangement, a slideable connection is provided. In this arrangement, a rod 332 is provided between the bearing housing 228 and the catheter body 120. The rod 332 can have any suitable configuration, but may have a proximal end configured to be received in a recess or lumen formed in the catheter body 120 and a distal end 340 configured to couple with the bearing housing 228. FIG. 3 shows that the distal end 340 of the rod 332 can be configured to engage with a feature of the bearing housing 228 so that a limited range of sliding is permitted.

In one embodiment, the bearing housing 228 has an elongate channel 342 configured to receive a middle portion of the rod 332 and an enlarged depression 344 located at the distal end of the channel 342. The depression 344 has a width W that is sufficient to receive a wide distal end of the rod 332. The depression 344 can be configured to have an axial length along the housing 228 that can define a range of motion of the bearing housing 228 relative to the catheter body 120.

In one arrangement, the bearing housing 228 is positioned relative to the catheter body 120 and the rod 332 such that the distal portion of the rod 332 is located at the distal end of the depression 344. Thereafter, the catheter assembly 100 can be manipulated such that the bearing housing 228 moves distally relative to the catheter body 120 and the rod 332 such that the distal portion of the rod 332 is located at the proximal end of the depression 344. In the distal position, the impeller assembly 116 is located more distally than in the proximal position. As discussed further below, this enables a variety of techniques for unfurling the impeller blades 212 within the housing 202.

B. Bearing Configurations

Any suitable bearing can be used in the catheter assembly 100. The provision of an infusate for hydrodynamic support enables a wide range of bearing materials to be used. If saline or other more corrosive infusate is used, the bearing must be carefully configured to not degrade within the expected duty cycle of the pump 10. Some polymeric materials are advantageously not degraded by isotonic saline, and are acceptable materials from this perspective. Under the fluid-dynamic conditions, a hydrodynamic bearing that is supported by a biocompatible infusate such as isotonic saline is preferred. It is believed that certain polymer bearings in combination with isotonic saline can support such conditions as 35,000-50,000 psi-ft/min for an appropriate duty cycle. Other aspects that can guide the choice of bearing configurations include minimizing thermal expansion, given the heat that could be generated in the heart pump 10, and minimizing moisture absorption.

Any suitable polymeric material may be used for the bearings 232a, 232b. The polymeric material can include a homopolymer, a copolymer, or a mixture of polymers. The polymeric material can include thermoplastic or thermoset polymers. Examples of polymers that can be used for bearings 232a, 232b include, but are not limited to, one or more of a polyketone, a polyether, a polyacetal, a polyamide-imide, a polyacetal, polyether ether ketone (PEEK), polytetrafluoroethylene (PTFE), and polyphenylene sulfide (PPS).

The polymeric material can also include (e.g., can be mixed, combined, and/or filled with) one or more additives such as a reinforcer and a lubricant. Specific additives include, but are not limited to, graphite, carbon fiber, glass fiber, and PTFE. Those of ordinary skill in the art may appreciate that the additives may be polymeric or non-polymeric. In some embodiments, the polymeric material used for bearings 232a and/or 232b can include PEEK, carbon fiber, PTFE, and graphite. In other embodiments, the polymeric material can include PPS and glass fiber. In yet other embodiments, the polymeric material can include a polyamide-imide polymer, carbon fiber, and graphite. The polymeric material can include any suitable amount of additive(s). For example, the polymeric material can include a total amount of additive(s) in the range of from about 1 wt % to about 50 wt %, based on the total weight of the polymeric material. In other embodiments, the polymeric material used for bearings 232a, 232b may not include any additives.

The polymeric material chosen for bearings 232a, 232b can have particular characteristics that advantageously affect the performance of the bearings. For example, in order to minimize thermal expansion caused by the heat generated in the heart pump 10, a preferred material would be subject to a minimum of dimensional change, and can have a coefficient of thermal expansion in the range of from about $1.2 \times 10^{-5}$ ° F.$^{-1}$ to about $25.2 \times 10^{-5}$ ° F.$^{-1}$. In other embodiments, the polymer used for bearings 232a, 232b has a coefficient of friction in the range of from about 0.15 to about 0.3. In another example, in order to minimize or prevent water absorption, the selected polymeric material can have a water adsorption in the range of from about 0.01% to about 0.4% over a 24 hour period. In yet another example, the polymeric material can be suitable for high pressure and velocity performance, and can have a limiting pressure-velocity (PV) in the range of from about 20,000 psi-ft/min to about 50,000 psi-ft/min.

The polymeric material used for bearings 232a, 232b may be commercially available. Examples of suitable, commercially-available polymeric materials include, but are not limited to, Ketron PEEK-HPV, Turcite A, Turcite X, Turcite TX, Rulon LR, Rulon J, Rulon 641, Rulon AR, Techtron HPV PPS, Ryton PPS, Torlon 4301, and Torlon 4501. In some embodiments, the polymeric material used for bearings 232a, 232b is Ketron PEEK-HPV.

Of course, other bearing configurations and/or materials would be suitable under other conditions, e.g., with less corrosive infusates or if a hydrostatic or non-hydraulic bearing is used.

C. Torque Coupling Systems

A torque coupling system is provided to rotate the impeller 200 at a high rate to move blood from inside a heart camber to a location within a patient's vasculature in amounts sufficient to sustain the patient or provide treatment to the patient. The torque coupling system couples the impeller 200 with the motor 136, which may be disposed outside the patient. It is expected that the impeller 200 and the drive shaft 148 are to be rotated at 25,000-30,000 revolutions per minute for a period of seven to ten days. To provide reliable performance under these conditions, isotonic saline or other lubricant is provided between the drive shaft 148 and stationary components therearound.

FIGS. 11 and 4B illustrate proximal and distal portions 400, 404 of the drive shaft 148. The proximal portion is coupled with the drive assembly 146 such that rotation of the drive assembly 146 rotates the drive shaft 148. The distal portion 404 of drive shaft 148 is coupled with the impeller shaft 204 such that rotation of the drive shaft 148 causes rotation of the impeller shaft 204. The drive shaft 148 also includes an elongate body 408 that extends between the proximal and distal portions 400, 404. The elongate portion 408 comprises a lumen 412 extending therethrough.

The size of the elongate body 408 may be as small as possible to minimize the cross-sectional profile of the catheter assembly 100. The cross-sectional profile of the catheter assembly 100 corresponds to the crossing profile of the catheter assembly, which limits where the system can be inserted into the vasculature. The lumen 412 is sized to permit a guidewire to be advanced therethrough in some embodiments. The use of a guidewire is optional, but may simplify insertion.

In one embodiment, the elongate body 408 comprises a multi-layer construction. In some embodiments, each layer can include at least one coil wire or a plurality of coil wires all wound in a same orientation. For example, a two-layer, counter-wound wire construction is particularly advantageous. A first layer (e.g., an inner layer) of the elongate body 408 is provided by a coiled wire of nickel-molybdenum-chromium alloy, such as 35NLT or MP35N. In other embodiments, the wire material can be MP35N LT. In one embodiment, the wire has a 0.008 inch diameter and the coil has a 5 filar right-hand wound construction. The outer diameter of the first layer may be about 0.071 inch. A second layer (e.g., an outer layer) of the elongate body 408 can include the same material as the first layer, disposed on the outside of the first layer. The first and second layers can be wound in the same direction, or in opposite directions. For example, in some embodiments the first layer (e.g., an inner layer) can be left-hand wound and the second layer (e.g., an outer layer) can be right-hand wound, or vice versa. In other embodiments, both the first and second layers can be left-hand wound. In yet other embodiments, both the first and second layers can be right-hand wound. The wound coil wire construction can advantageously facilitate proximal and/or distal flow of infusate along the outer layer of the elongate body 408. For example, the outer layer can be constructed such that the infusate travels along the coil and/or in the direction of the winding. Those skilled in the art may appreciate that, depending on the direction of rotation of the elongate body 408, the infusate flow can advantageously be directed either proximally or distally. The second layer may be a 5 filar left-hand wound construction. In one embodiment, each layer is formed using a 0.008 inch diameter wire, in the above-noted coiled configuration. In other embodiments, the elongate body 408 can include three or more coil wire layers, wherein the layers are wound in alternating directions. In some embodiments, the outer diameter of the second layer can be between about 0.072 inch and about 0.074 inch, while in other embodiments the diameter can be much larger or smaller. In some aspects, for example, the outer diameter of the second layer can be about 0.073 inch. The inner diameter of the elongate body 408 can be at least about 0.039 inch in some implementations. In some embodiments, one or more ends of the elongate body 408 can be welded and square cut, for example, with a 0.1 inch maximum weld length on each end. The length of the elongate body 408 can vary, but in some embodiments, the length can be between about 47 inches and 48 inches, for example, about 47.5 inches.

Other materials and other constructions are possible. The elongate body 408 can be made of other non-ferrous metals or other corrosion resistant material or constructions with appropriate modulus. Other materials that could meet the corrosion requirements include stainless steel (e.g., 302, 304, or 316). In certain embodiments, the elongate body 408 can have a structure that enables other materials to be used. For example varying at least one of coil layers, filars, wire diameter, and coil diameter may enable an otherwise less robust material to operate below the fatigue stress of that material.

In another embodiment, a four layer construction is provided. The four layers comprise three wire-wound layers, e.g., similar to the arrangement described above, but included a third wound layer on the outer surface of the second layer. A low friction layer can be disposed on the outside surface of the elongate body 408. One material that could be used as a low-friction layer is PTFE, known commercially as Teflon®. The low-friction layer should be configured to have sufficient wear resistance, such as by selection of the appropriate PTFE material, e.g. polyphenylene sulphone-filled PTFE, and/or by insuring appropriate infusate flow is maintained during the entire duration of use of the device in order to prevent undesirable local elevated temperature of the PTFE material.

The drive shaft 148 operates within the multilumen catheter body 120. Because the drive shaft 148 is rotated at a very high rate when in use within the multilumen catheter body 120, the configuration of the surface forming the central lumen 286 is important. In some embodiments, this inner surface has high lubricity and high wear resistance. One material that can be used for the inner surface of the catheter body 120 is high density polyethylene (HDPE), which provides sufficient lubricity and wear resistance. In one embodiment, the entire multilumen catheter body 120 is formed of HDPE. PTFE provides good lubricity and could be used if made sufficiently wear resistant. One way to increase the wear resistance of PTFE is to impregnate it with polyphenylene sulphone ($PPSO_2$), another is to gamma irradiate the material. One way to increase the lubricity of Polyimide materials is to impregnate it with Graphite, another is to impregnate it with Graphite and PTFE.

FIG. 4B shows a clearance 412 between the elongate body 408 of the drive shaft 148 and the inner surface of the multilumen catheter body 120. The clearance 412 may be about 0.005 inch. Along a diameter between opposite sides of the inner surface of the central lumen 286 and outer surface of the elongate body 408 includes about 0.010 inch of space or diametric clearance. A larger minimum clearance may be desirable if the crossing profile can be enlarged or if other structures of the catheter assembly 100 can be made thinner or eliminated to allow more room between the elongate body 408 and the central lumen 286.

FIGS. 11 and 12 show further details of the drive assembly 146, which is disposed at the proximal end 104 of the catheter assembly 100. The drive assembly 146 includes a drive housing 450 having a recess or cavity 454 disposed therein. The cavity 454 is configured for mounting a rotor support shaft 458 for rotation therein. The support shaft 458 has a proximal end and a distal end and a plurality of components mounted thereon. The distal end of the support shaft 458 has a recess 462 formed therein to receive a proximal end of the drive shaft 148. The support shaft 458 may also have a lumen 466 disposed therein for slideably receiving a guidewire.

A rotor 470 is mounted on an outer surface of the support shaft 458 between sleeve bearings 474a, 474b, as shown in FIG. 12. The rotor 470 can take any suitable form, but in one embodiment includes an elongate magnet 476 disposed between proximal and distal flywheels 478a, 478b.

The proximal end of the support shaft 458 has a tapered port 480 for receiving the guidewire. The proximal end can be configured for engaging the motor 136 in some embodiments. In other embodiments, a magnetic field is induced by the motor 136 in a manner that creates torque and rotation of the shaft 458.

An infusate outflow path 482 is provided within the drive assembly 146. The outflow path 482 is provided between an outer surface of the support shaft 458 and an inner surface 486 of the distal bearing. The flow path 482 continues from the distal bearing 474b radially outwardly along thrust surfaces 490a. The flow path continues proximally between the outer surface of the rotor 470 and the inner surface defining the cavity 454. The flow path 482 continues radially inwardly along the thrust surface 490a toward the support shaft 458. The flow path 482 continues proximally between the support shaft 458 and the proximal bearing 474a. Proximal of the bearing 474a, the flow of infusate exits the catheter assembly 100 through an outflow port 144 through which it can be directed to the waste container 46 or discarded. The flow path is shown in more detail in FIGS. 1, 12, 12A, and 12B.

III. Structures that Facilitate Deployment and Retrieval

The catheter assembly 100 can include one or more features that facilitate the deployment and/or retrieval of one or more components of the distal end 108 of the heart catheter assembly 100 (e.g., the impeller assembly 116 or a portion thereof). The catheter assembly 100 can be used in conjunction with any of the pumps, catheter assemblies, systems, or components thereof disclosed in U.S. Pat. Nos. 8,992,163; 8,535,211; 9,138,518; 8,597,170; 8,485,961; 8,591,393, in U.S. Patent Publication Nos. 2013/0066140; 2013/0303970; 2014/0275725; 2013/0303969; 2015/0099922; 2014/0012065; 2014/0010686; 2014/0275726; 2015/0290372; 2015/0290371, in U.S. Application No. 61/979,876; 61/979,925; 61/979,937; 62/038,678; Ser. Nos. 15/003,576; 15/003,682; 15/003,696, or in International Publication Nos. WO 2015/160942; WO 2015/160980; WO 2015/160990; WO 2016/028644, the contents of each of which are hereby incorporated by reference herein in their entirety and for all purposes.

A. Catheter Assembly with Position and/or Orientation Holding Brace

Figure 13:
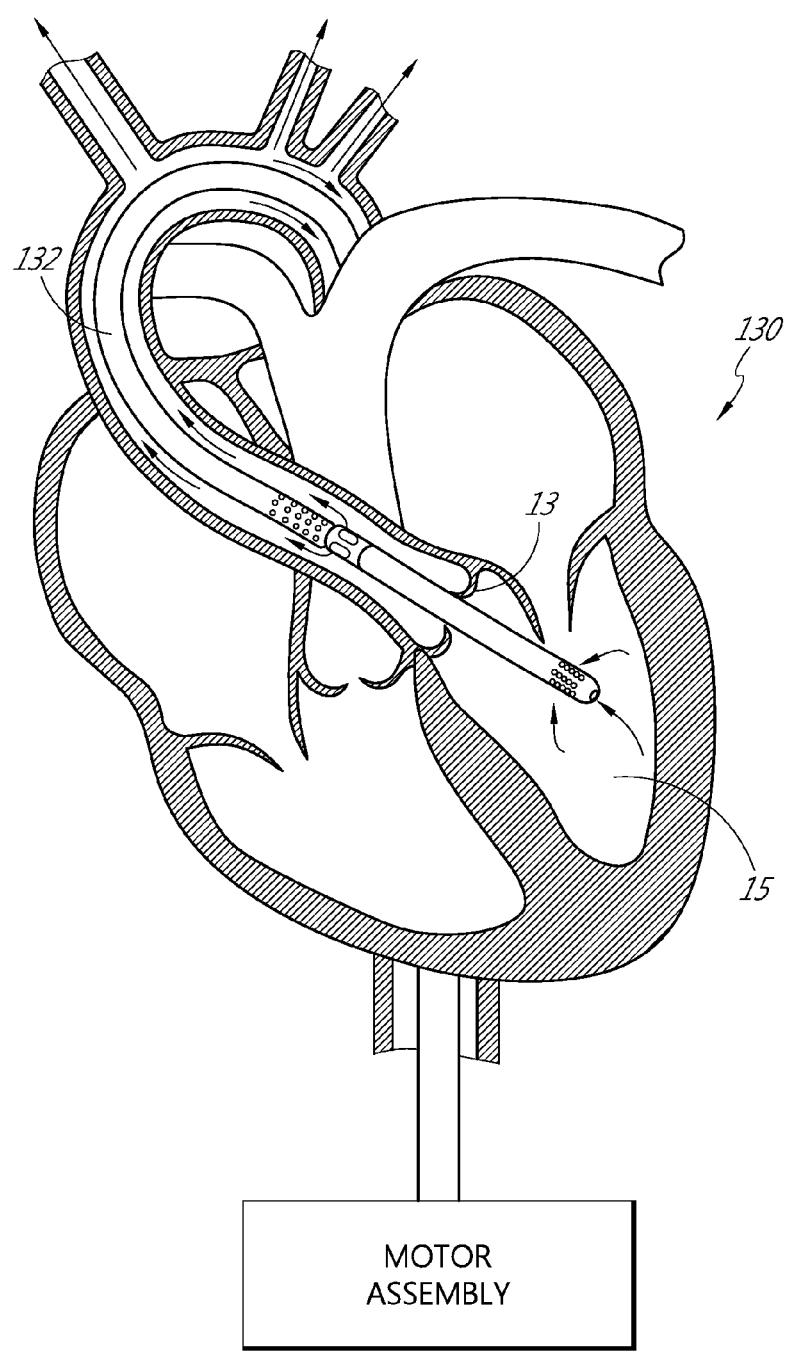
FIG. 13 illustrates a prior art technique for placing a prior art catheter pump.
Figure 14:
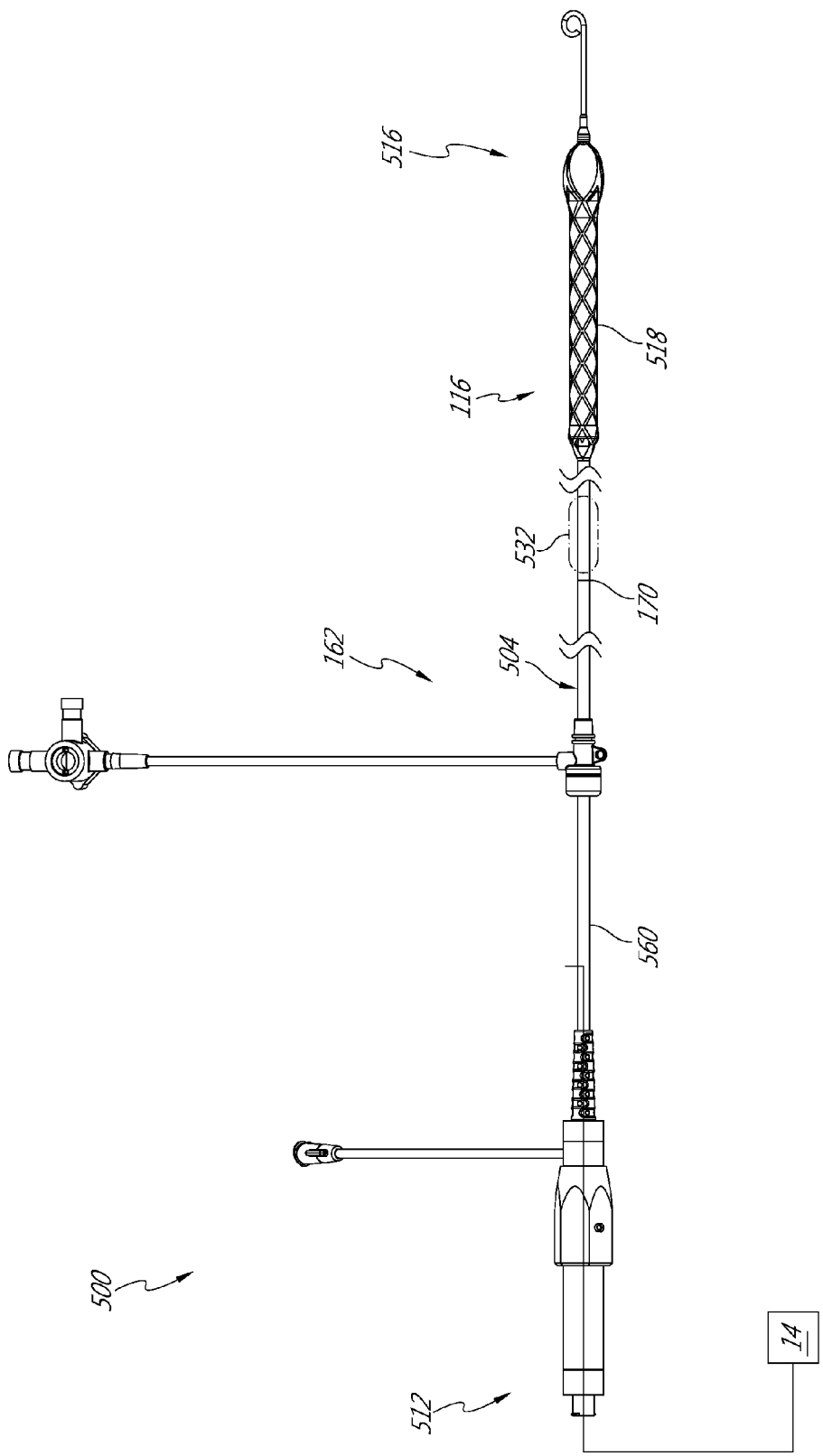
FIG. 14 is a plan view of one embodiment of a catheter assembly adapted to be used with the heart pump of FIG. 1.

FIG. 13 shows a prior art catheter system with a guide catheter 132 of a pump system 130. As discussed above, the pump system 130 is under several distinct loads in operation. The heart is continually beating and is physically contacting the pump system 130 at least at the aortic valve 13 in every heartbeat. The fluid pressures in the left ventricle 15 and in the aorta 13 differ and also vary over time. The system typically generates some axial loads in response to the pumping of fluid. Though these axial loads are applied to the system in FIG. 13, there is no structure or method in the system 130 of FIG. 13 to maintain the position of the pump under these conditions. FIGS. 14-15C illustrate intravascular structures and methods that stabilize the position of the working end of a catheter pump and minimize or reduce tip gap variability in a cannula of a percutaneous pump with an expandable impeller.

FIG. 14 show a catheter assembly 500 that is similar to the catheter assembly 100 except as discussed below. The catheter assembly 500 can be combined with a controller and the various other components of a catheter pump disclosed herein. The catheter assembly 500 includes a catheter body 560, an elongate body 504 disposed about the catheter body 560, a shaft 508, and an impeller assembly 116 comprising an impeller 510 connected to the shaft 508 (see FIG. 15B). The impeller 510 operates within a cannula 518 that carries blood from a heart chamber (or other source of blood) to a blood vessel such as the aorta or pulmonary artery in a ventricular support context. The catheter assembly 500 has a proximal end 512, a distal end 516 and at least one lumen extending therebetween. The lumen is not shown but is similar to the lumen 286 shown in FIG. 7. The shaft 508 (shown in FIG. 15B) is disposed at least partially within the elongate body 504, e.g., in at least one lumen of the catheter body 560. The shaft 508 is journaled for rotation in the lumen. The impeller 510 is coupled with a distal portion of the shaft 508 (see FIG. 15B). The impeller 510 is configured to induce flow of blood when the impeller 510 is rotated in fluid communication with a source of blood. For example, a proximal end of the shaft 508 can be connected to a motor (such as the motor 14), which can rotate the shaft 508 and, in turn, the impeller 510.

An exemplary anchor comprising an inflatable balloon brace 532, shown schematically in FIGS. 14-14A and 15B-16, is disposed on an outer surface of the catheter pump or the catheter assembly 500. The inflatable balloon brace 532 is spaced proximally of the impeller 510. The inflatable balloon brace 532 has a low profile configuration for delivery through the vasculature and an expanded configuration for disposing (e.g., positioning and/or orienting) the impeller 510 within the heart or other source of blood. The exemplary anchor (e.g. balloon brace) is configured to expand against the adjacent tissues walls such as the inner walls of the aorta. For example, the balloon brace 532 may be expanded in a manner similar to that used for balloon pumps and/or stents. In some arrangements, an inflation lumen can be provided in the catheter assembly 500 which provides fluid communication between the interior of the balloon brace 532 and an inflation system. The inflation system can supply a fluid (any suitable gas, such as helium, etc.) to the balloon brace 532 by way of the inflation lumen to cause the balloon brace 532 to expand. In various embodiments, the anchor is configured to minimize restriction of blood flow when expanded. In various embodiments, the anchor is configured to allow blood to flow past the anchor. The brace 532 in the expanded configuration can maintain the impeller 510 in a desired pumping location relative to the heart (e.g., within the left ventricle 15 and/or disposed across the aortic valve 13) in the presence of forces imparted on the catheter assembly 500 during pumping.

Figure 14A:
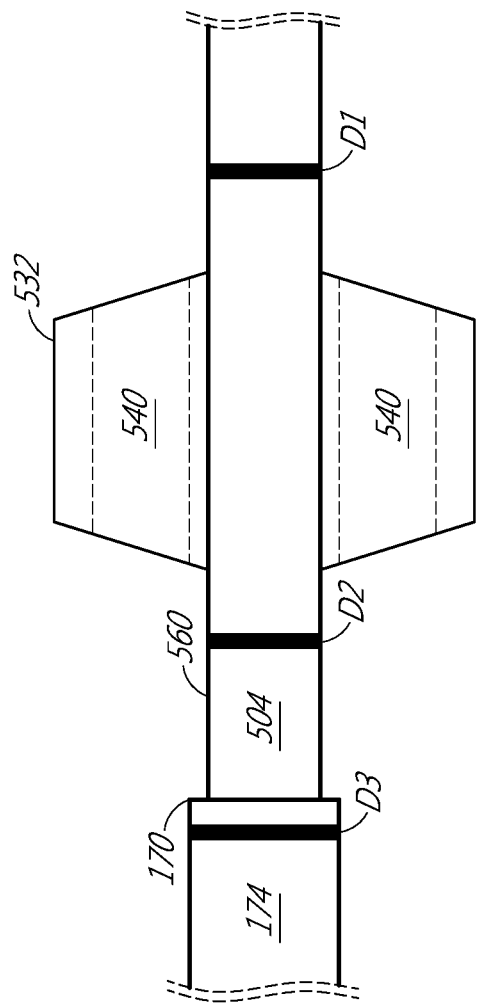
FIG. 14A is an enlarged view of a portion of the catheter assembly of FIG. 14 showing one embodiment of a balloon brace.

FIGS. 14A-14B show that the balloon brace 532 can be disposed closer to the distal end 516 than the proximal end 512. FIG. 15C shows that the location of the balloon brace 532 can enable the brace to be expanded in the vasculature close to the heart when the distal end 516 is disposed in the heart, e.g., in the left ventricle 15. In one embodiment, the balloon brace 532 is configured to be disposed adjacent to or in the aortic arch as shown in FIG. 15C. The balloon brace 532 can be disposed on the elongate body 504 such that when the elongate body 504 is inserted through a peripheral vascular location (e.g., a femoral artery) and advanced to the left ventricle the balloon brace 532 is disposed in the ascending aorta. Locations in the ascending aorta where the balloon brace 532 can be disposed include adjacent to, e.g., just upstream of, the brachiocephalic artery. In certain embodiments, the balloon brace 532 is disposed on the elongate body 504 such that when expanded the balloon brace 532 is disposed closer to the brachiocephalic artery than to the coronary arteries. In certain embodiments, the balloon brace 532 is disposed on the elongate body 504 such that when expanded the balloon brace 532 is disposed downstream of the coronary arteries by at least about 2 cm. In certain embodiments, the balloon brace 532 is disposed on the elongate body 504 such that when expanded the balloon brace 532 is disposed downstream of the coronary arteries by at least about 4 cm.

In other embodiments, the catheter assembly 500 is configured such that the balloon brace 532 is positioned on the elongate body 504 such that when the elongate body is inserted through a peripheral vascular location (e.g., a femoral artery) and advanced to the left ventricle, the balloon brace 532 is disposed in the descending aorta. For example, the balloon brace 532 can be disposed on the elongate body 504 such that when expanded the balloon brace 532 is disposed downstream of the subclavian artery by an amount likely to avoid blocking or jailing the subclavian artery. For example, the brace 532 can be expanded at least about 20 mm from the subclavian artery ostium. In other techniques, the brace 532 can be expanded at a location no closer than 40 mm from the subclavian artery. In other techniques, the brace 532 can be expanded at a location between the subclavian artery and any of the abdominopelvic branches. For example, a target zone can be defined as a zone including the longitudinal mid-point of the portion of the aorta extending between the subclavian and celiac arteries, the target zone having a length of no more than about one-half the distance between the subclavian and celiac arteries. A target zone can be defined as a zone including the longitudinal mid-point of the portion of the aorta extending between the subclavian and celiac arteries, the target zone having a length of no more than about one-quarter the distance between the subclavian and celiac arteries. A target zone can be defined as a zone including the longitudinal mid-point of the portion of the aorta extending between the subclavian and celiac arteries, the target zone having a length of no more than about 15% of the distance between the subclavian and celiac arteries. A target zone can be defined as a zone including the longitudinal mid-point of the portion of the aorta extending between the subclavian and celiac arteries, the target zone having a length of no more than about 10% of the distance between the subclavian and celiac arteries.

The balloon brace 532 can be disposed on the elongate body 504 such that when expanded the balloon brace 532 is disposed downstream of the subclavian artery by at least about 20 mm. The balloon brace 532 can be disposed on the elongate body 504 such that when expanded the balloon brace 532 is disposed downstream of the subclavian artery by at least about 40 mm.

The balloon brace 532 is configured to reduce obstructions of the flow or only minimally obstruct flow in the vasculature where the balloon brace is positioned. The balloon brace 532 can be configured with one or more flow-through channels 540 disposed therein. In various embodiments, the flow-through channels or similar features are configured to allow substantially all of the blood flow through the anchor. The flow-through channels 540 can be bounded by the balloon brace 532 in part and by the elongate body 504 in part. In other embodiments, the flow-through channels 540 can be bounded in part by the vasculature and in part by the balloon brace 532 when the catheter assembly 500 is disposed in the vasculature and the balloon brace 532 is expanded. For example, in other embodiments, the balloon brace 532 can have an outer perimeter with at least one concave portion such that a flow-through channel can be defined between the concave portion and the vessel wall. This embodiment is useful in allowing more flexibility in the placement of the balloon brace 532. For example, when the balloon brace 532 is configured to allow flow between the brace and the wall, the balloon brace can be placed at the same longitudinal position as a branch vessel. For example, in certain embodiments the balloon brace 532 can be disposed on the elongate body 504 such that when expanded the balloon brace 532 is disposed in the aortic arch, e.g., between the subclavian and brachiocephalic arteries without posing a risk to the flow in the branch vessels in that location. Although described in terms of flow-through channels, one will appreciate from the description herein that other features may be employed to allow blood to pass by or through the anchor and minimize disruption of the flow.

The portion of the cross-section of the blood vessel obstructed by the anchor (e.g. balloon brace 532) is less than 50 percent in some embodiments. In various embodiments, the anchor is configured to obstruct less than 25 percent of the cross-section of the vessel. In various embodiments, the anchor is configured to obstruct less than 15 percent of the cross-section of the vessel. In other embodiments, the portion of the cross-section of the blood vessel obstructed by the balloon brace 532 is less than 40 percent. In other embodiments, the portion of the cross-section of the blood vessel obstructed by the balloon brace 532 is preferably between about 10 percent and about 30 percent. In other embodiments, the portion of the cross-section of the blood vessel obstructed by the balloon race 532 is preferably between about 5 percent and about 15 percent.

FIG. 15C shows that the balloon brace 532 can be configured as a torus 552 in at least the expanded state. The torus 552 has an outer periphery that is adapted to contact an inner wall of a blood vessel, such as a portion of the aorta. The torus 552 has an inner periphery that in one embodiment surrounds a portion of the flow-through channel(s) 540. The torus 552 can have any cross-section that is symmetrical about an axis of revolution. In such embodiments, the elongate body 504 can be disposed between the inner periphery of the torus 552 and the axis of revolution of the torus 552. This provides an off-set position for the elongate body 504 which in part positions the body 504 closer to the superior internal wall of the aorta near the brachiocephalic artery in one embodiment.

Expansion of the torus 552 can be by any suitable structure or mechanism. In one embodiment, an inflation channel 556 is provided between the torus 552 and an inflation lumen disposed in the elongate body 504, e.g., within the catheter body 560. The inflation lumen can be disposed in a peripheral position, e.g., as one of or in the position of the lumens 282 (see FIG. 7). The inflation channel 556 can have a space that is fluidly coupled with an interior space of the torus 552 and with the inflation lumen. The inflation channel 556 can be disposed in one or more arms extending from the elongate body 504 to the torus 552.

In one embodiment, the balloon brace 532 is configured to deform and conform to the shape of the portion of the aorta in which the balloon brace is disposed when the catheter assembly 500 deployed in the patient. The deformation of the balloon brace 532 increases the surface area of contact between the balloon brace 532 and the aorta 13 (or other vascular segment in which it is disposed) to increase the secure connection between the catheter assembly 500 and the aorta 13 (or the vascular segment). The balloon brace 532 can also be asymmetric to enhance engagement with the aorta 13 (or the vascular segment). For example the balloon brace 532 can be asymmetric to a plane perpendicular to the longitudinal axis of the elongate body 504. The asymmetry of the balloon brace 532 can provide a wedge-like configuration in the expanded state of the balloon brace.

FIGS. 14A-14B show that the balloon brace 532 can be disposed on an outer surface of a catheter body 560 similar to the catheter body 120. The brace 532 can be disposed between the catheter body 560 and an inner surface of the sheath assembly 162 in a delivery configuration (e.g., in a collapsed configuration). The brace 532 can be exposed by withdrawing the sheath assembly 162 until the distal end 170 of the sheath assembly is proximal of the balloon brace.

In other embodiments, the balloon brace 532 can be disposed on the sheath 162 and thus can be moveable relative to the elongate body 504 and the impeller 510. This enables the clinician to change the relative position of the balloon brace 532 in the vasculature to selectively optimize the deployment of the pump including the catheter assembly 500. For example, the clinician can elect to place the balloon brace 532 upstream or downstream of the aortic arch. The clinician can move the balloon brace 532 to any position within the ascending or descending aorta. This provides a great degree of flexibility in the selection of the vascular location for bracing the working end.

FIG. 14A is a close-up version of a portion of the catheter assembly 500 showing visualization devices D1, D2, D3 provided to assist in the positioning of the balloon brace 532. FIG. 14B shows these same devices used in connection with mechanically deployable braces 532A. For example, a distal visualization device D1 can be disposed at a location just distal of the brace 532, 532A to indicate the position of the brace, e.g., that when expanded the brace 532, 532A will be just proximal to the device D1. The visualization device D1 can be a radiopaque marker, such as a metallic band or zone disposed about the catheter body 560. The visualization device D1 can be or can include a port for egress of contrast fluid from the catheter body 560. In one embodiment, a proximal visualization device D2 can be disposed at a location just proximal of the brace 532, 532A to indicate the position of the brace, e.g., that when expanded the brace 532, 532A will be just distal to the device D2. The visualization device D2 can be a radiopaque marker, such as a metallic band or zone disposed about the catheter body 560. The visualization device D2 can be or can include a port for egress of contrast fluid from the catheter body 560. In one embodiments, only the proximal device D2 is provided. In one embodiments, only the distal device D1 is provided. In one embodiment, both proximal and distal visualization devices D1 and D2 are provided.

FIG. 14A shows that the proximal device D2 can be disposed at a selected location relative to the location of the distal end 170 of the sheath assembly 162 when the sheath assembly is proximal of the balloon brace 532. For example, the brightness of the device D2 can appear the same as that of the mark D1 indicating that the distal end 170 is proximal of the device D2 as shown. The brightness of the device D2 can appear less than that of the mark D1 indicating that the distal end 170 is distal of the device D2 (or between the devices D1, D2 if both present). In one embodiment the device D3 is disposed on the elongate body 174 of the sheath assembly 162. Thus the device D3 indicates position of the distal end 170 relative to the balloon brace 532 if the balloon brace is disposed on the elongate body 504 of the catheter assembly 500. In this embodiment, the devices D1 and D2 may be omitted.

FIG. 14A illustrates an embodiment in which three or more visualization devices are provided on the catheter assembly 500. For example, the devices D1, D2 can be disposed on the elongate body 504 just distal to and proximal of (respectively) the balloon brace 532 (or mechanical brace 532A as in FIG. 14B). A third visualization device D3 can be disposed on the elongate body 174 of the sheath assembly 162. Thus, real-time information about the proximal-distal location of the balloon brace relative to the anatomy and of the distal end 170 of the sheath assembly 162 relative to the brace can be ascertained.

In another embodiment, a plurality of brace structures is provided. For example, a brace can be provided on both the elongate body 504 and the sheath 162. This enables the clinician to decide which portion of the catheter assembly 500 will best be braced. This also enables the clinician to decide to brace both the elongate body 504 and the sheath 162.

FIG. 14B illustrates an anchor comprising a brace 532A, according to another embodiment. The brace 532A can be mechanically deployed rather than using an inflation medium. The brace 532A comprises a plurality of petals or lobes 564 that can extend outwardly from an outer surface of the elongate body 504. The lobes 564 can include arcuate portions 568 that are configured to be deployed and come to rest on a vascular surface. For example each lobe 564 can include a convex outer curvature 570 that can atraumatically rest on the endothelial lining of the aorta 13. For example, the brace 532A can be configured such that apex of the curvature 570 is disposed away from the central longitudinal axis of the body 504 by a distance greater than the average radius of the vessel segment where the brace 532A is to be deployed. However, the gentle slope of the convex outer curvature 570 enables any position along a range on either side of the apex to engage the vessel wall to provide secure engagement. The brace 532A can thereafter anchor a distal portion of the catheter assembly 500 within the patient from a location in the vasculature.

The lobes 564 are configured to be compressed within the sheath assembly 162 during delivery and withdrawal of the catheter assembly 500. For example, relative distal movement of the distal end 170 of the sheath assembly 162 over an inclined portion 572 of the brace 532A can urge the lobes 564 inwardly (relative to the central longitudinal axis of the body 504).

In the illustrated embodiment, the brace 532A includes four lobes 564. First and second lobes 564 disposed above and below the elongate body 504 are partially shown in cross-section. As second mirror image portion of the first and second lobes 564 would extend out of the page between distal portions 574 (shown in cross-section) and the inclined portion 572 (also in cross-section). A third lobe 564 is disposed in part behind the elongate body 504 in the view of FIG. 14B. The third lobe 564 has first and second arms 576 that are symmetrical about a plane intersecting the central longitudinal axis of the elongate body 504 and the distal portion 574 of the third lobe. The fourth lobe is not shown but is symmetrical to the third lobe, e.g., coming out of the page in the image of FIG. 14B. The brace 532A can comprise a shape memory material such as a nickel-titanium alloy (e.g., nitinol), spring steel or other highly elastic material or structure. As such, the brace 532A can be compressed inside the sheath assembly 162 and expanded as illustrated in FIG. 14B multiple times. While FIG. 14B illustrates one example of a mechanically deployable brace, the mechanically deployable brace 532A can take any other suitable configuration.

B. Sheath Having Expandable Distal End

As described herein, the pump can include a sheath assembly. The sheath assembly can control the collapse and expansion of the impeller and/or the impeller housing. In some embodiments, the distal end of the sheath assembly can optionally include one or more structures that aid in the deployment and/or retrieval of the impeller assembly. Such structures can be configured to be extended over the balloon brace 532 to retrieve the balloon brace after it has been expanded.

In some embodiments, as shown in FIGS. 17A to 17D, the sheath assembly can include an expandable distal end 170*a*, 170*b*, 170*c*. For example, the distal end can expand when a radial force is applied, and can contract when the radial force is removed. The distal end may also be able to expand and/or contract repeatedly. When expanded, the distal end 170*a*, 170*b*, 170*c* can have a conical and/or funnel-like configuration. When not expanded, the distal end 170*a*, 170*b*, 170*c* can have a generally cylindrical (e.g., generally constant diameter) configuration, for example as illustrated in FIG. 17A. To assist with expansion and/or contraction, the distal end 170*a*, 170*b*, 170*c* or portions thereof may be made from materials having a different flexibility and/or elasticity (e.g., more or less flexible and/or elastic) than the material(s) used for all or a portion of the remainder of the sheath assembly. In some embodiments, the sheath assembly 162 can have at least one configuration where it is at least partially disposed over the impeller housing, catheter assembly, and/or impeller assembly. Advantageously, the conical and/or funnel-like configuration can aid the deployment and/or retraction of the impeller assembly and/or impeller housing as described herein as well as the balloon brace 532 and variations thereof.

As illustrated in FIG. 17A, the distal end 170*a* can include one or more axial slits 702 (e.g., 2, 3, or 4 slits). Slit 702 can extend proximally from the distal end 170*a* at least partially along the length of the elongate body 174. The distal end 170*a* can also include a plurality of elongate members 704 (e.g., 2, 3, or 4 elongate members). Each elongate member 704 can be joined at one end (e.g., proximal end) to the sheath assembly. Each elongate member 704 can also have a distal end 705 that is outwardly deflectable away from axis 708. The elongate members 704 can be separated from each other by the slits 702. Each elongate member 704 can have a width that is defined by the distance between slits 702 and a length defined by the length of each adjacent slit 702. In some embodiments, the elongate members 704 and slits 702 can be generally equally spaced circumferentially about the elongate body 174. In some embodiments, the elongate members 704 can each have a length that is generally equal to or greater than the axial length of the outlet portion of the impeller housing. For example, in some embodiments, the elongate members 704 can each have a length in the range of from about 0.25 in. up to about 2.0 in. In other embodiments, the elongate members 704 can each have a length in the range of from about 0.5 in to about 0.75 in. The elongate members 704 and/or at least a portion of the sheath assembly 162 (e.g., the portion of the sheath assembly 162 that connects to elongate members 704) can be made from a relatively elastic material (e.g., any of the elastomeric polymers described herein).

In use, an outwardly-acting radial force resulting from the radial stiffness of the impeller housing can be applied to the elongate members 704 which causes the elongate members 704 to deflect outwards, as illustrated in FIG. 17B. For example, the axial movement of the impeller housing in the proximal direction into the sheath assembly (or distal movement of the sheath over the expanded impeller housing) can cause the elongate members 704 to deflect outwards. The outward deflection of the elongate members 704 can result in the conical or funnel-like configuration of the distal end 170*a* when sheathed over an expanded section of the impeller housing. When the elongate members 704 are deflected outwards, the width of each slit 702 can increase at the distal end to define a gap 709. In some embodiments, the elongate members 704 can be self-collapsing. For example, the elongate members 704 can be configured to return to their original configuration when the internal outward-acting radial forces are released (e.g., where the elongate members 704 are made of a relatively elastic material).

As illustrated in FIG. 17C, the distal end 170*b* of the sheath assembly can include an deformable structure 706 (e.g., a webbing) that at least partially covers one or more slits 702. In some embodiments, the deformable (e.g., stretchable, expandable, flexible, and/or elastic) structure 706 can surround, coat, and/or cover at least a portion of the distal end 170*b* (e.g., the elongate members 704). As illustrated in FIG. 17C, the deformable structure 706 can be an elastomeric coating (e.g., incorporating those elastomeric materials described herein). In other embodiments, the deformable structure 706 can include a spring, such as a semi-circular spring member having a straight or oscillatory pattern. In use, the deformable structure 706 can be configured to return the elongate members 704 to their original, non-conical configuration and/or prevent over-deflection of the elongate members 704 beyond their elastic limit.

In some embodiments, the elongate members 704 can be stiffer (in the circumferential and/or axial direction(s)) than the proximally-adjacent portion of the sheath assembly. Advantageously, the stiffer material can prevent or inhibit the distal-most end of the sheath assembly from folding over itself when it encounters resistance (e.g., advancing the sheath over an expanded cannula housing). In one embodiment, one or more elongate members 704 can be reinforced with a plurality of wires that extend to the distal-most tip of the elongate member 704. In another embodiment, one or more elongate members 704 can be made from a polymer that is stiffer than the material (e.g., a second polymer) of the proximally-adjacent portion of the sheath assembly.

As illustrated in FIG. 17D, in some embodiments the distal end 170c of sheath assembly 162 can include an integral funnel 710 having a distal, conically-shaped portion 711. As described further herein, the integral funnel 710 can be expandable and/or collapsible. Advantageously, the integral funnel 710 can assist in deployment and retraction of the housing while minimally increasing the profile of the pump. The integral funnel 710 can be connected to a non-expandable portion 712 of the sheath, for example, at a distal-most tip 714. The integral funnel 710 can include an outer layer 713 and an inner layer 715 that converge at an interface 717. The integral funnel 710 can be layered over an outer surface 716 and over an inner surface 718 of the non-expandable portion 712. Accordingly, as illustrated in FIG. 17D, at least a portion of the inner layer 715 can reside, at least temporarily, within the lumen of the sheath assembly 162. The integral funnel 708 can be connected to either the outer surface 716 or the inner surface 718 of the sheath. In some embodiments, the funnel 710 can be a distal extension of distal end 170 that is folded over the non-expandable portion 712.

The integral funnel 710 can be slideable over the outer surface 716 and/or the inner surface 718 of the non-expandable portion 712. The contact surfaces between the non-expandable portion 712 and the integral funnel 710 and/or between the outer layer 713 and the inner layer 715 can be lubricated, e.g., using a silicone lubricant, to establish and/or maintain slideability and/or low friction. The integral funnel 710 can be made from a thin, flexible material, such as a polyurethane polymer. In some embodiments, the integral funnel 710 can be made from a material that is more flexible and/or elastic than the material that is used for all or a portion of the remainder of the sheath assembly. In some embodiments, the material used for the integral funnel 710 can have one or more membrane-like qualities. In use, the axial movement of the housing 202 (not shown) can frictionally engage the integral funnel 710, causing the integral funnel 710 to deploy or retract. For example, in embodiments where the outer layer 713 is affixed to the non-expandable portion 712 of the sheath, axial movement of the housing 202 in a distal direction can cause the inner layer 715 to translate distally (e.g., slide distally along the inner surface 718 of the sheath), thus deploying the conical portion 711 (e.g., pulling the conical portion 711 out of the sheath). Axial movement of the housing in a proximal direction can cause the inner layer 715 to translate proximally (e.g., slide proximally along the inner surface 718 of the sheath), thus retracting the conical portion 711 into the sheath (e.g., pulling the conical portion 711 into the sheath). The thin, flexible material of the conical portion 711 can advantageously allow the conical portion 711 to deform upon retraction of the balloon brace 532 and the housing into the sheath.

In embodiments where the inner layer 715 is affixed to the non-expandable portion of the sheath, axial movement of the housing 202 can cause the outer layer 713 to translate. For example, distal movement of the housing can cause the outer layer 713 to slide distally along the outer surface 716 of the sheath. Proximal movement of the housing can cause the outer layer 713 to slide proximally along the outer surface 716 of the sheath.

In some embodiments where the funnel 710 is a distal extension of the non-expandable portion 712 that is folded over the non-expandable portion 712, the funnel 710 can slide distally as the non-expandable portion 712 is moved proximally. In use, as the non-expandable portion 712 is moved proximally, the funnel 710 can slide distally to unfold and surround the balloon brace 532 and/or the impeller assembly 116.

IV. Methods

Various methods and techniques are discussed above in connection with specific structures of heart pumps. The following elaborates on some aspects of these techniques and methods. The following discussion is to be read in light of and freely combined with the foregoing discussion.

A. Retracting and Deploying the Impeller Housing by Way of the Impeller Deployment Assembly at the Proximal End of the Catheter Body As discussed above, in various embodiments the heart pump 10 is inserted in a less invasive manner, e.g., using techniques that can be employed in a catheter lab. Various general techniques pertinent to the heart pump 10 are described in U.S. patent application Ser. No. 12/829,359, filed on Jul. 1, 2010, and entitled Blood Pump With Expandable Cannula, which is incorporated by reference herein in its entirety and for all purposes.

Because the catheter assembly 100 or the catheter assembly 500 is to be delivered through a small access site, it can be important to ensure that the impeller housing is reliably deployed and retracted, as described above. A clinician may begin a heart pumping procedure by introducing the catheter assembly 100 or the catheter assembly 500 into the patient percutaneously, e.g., by urging the catheter assembly through the femoral artery and into a heart chamber. Because the impeller and impeller housing are advanced through a narrow artery in some embodiments, the impeller and impeller housing can initially be inserted into the patient in a retracted, or collapsed (or low profile), state, as described above. Once the distal end of the catheter assembly 100 or the catheter assembly 500 (including their respective impeller housings) has reached the desired operating location (e.g., a heart chamber), the clinician can deploy the impeller housing into an advanced or expanded configuration. Either before or after deploying the impeller housing of the catheter assembly 100 or the catheter assembly 500 a technique can be used to control the position of the impeller housing and/or the magnitude of variation in tip gap between the housing and the impeller.

1. Superior Aorta Wall Positioning Techniques

As noted above, it is preferred to reduce or minimize variation in tip gap within the impeller assembly 116. One technique is to maintain a distal portion of the catheter assembly 100 (e.g., including the impeller assembly 116 and a length of the catheter assembly proximally thereof) as straight as possible. Within the anatomy, a substantially straight trajectory is defined from a superior portion of or position within the aortic arch adjacent to the brachiocephalic artery, across the aortic valve, and into the left ventricle. The catheter assembly 100 can be positioned such that a distal portion thereof follows this straight trajectory.

In order to position the distal portion in this manner, the catheter assembly 100 is inserted into the femoral artery and advanced retrograde over the aortic arch and across the aortic valve. The catheter assembly 100 is generally delivered over a guidewire to this position. Once positioned, the guidewire can be withdrawn and removed. Thereafter, the catheter assembly 100 is then positioned superiorly within the aortic arch such that an intermediate portion of the catheter assembly 100 extending through the aortic arch is placed in contact with the superior surface or aspect of the aortic arch. A portion of the catheter assembly 100 distal the aortic arch is maintained straight through the ascending aorta and the aortic valve. The portion can extend from just upstream of the brachiocephalic artery. For example, contact with the superior aspect of the aorta can begin at within about 20 mm of the brachiocephalic artery and can extend generally in contact with the aortic arch throughout the aortic arch.

In other techniques, the brace 532 can be expanded at a location between the brachiocephalic artery and the aortic valve. For example, a target zone can be defined as a zone including the longitudinal mid-point of the portion of the aorta extending between the brachiocephalic artery and the aortic valve, the target zone having a length of no more than about one-half the distance between the brachiocephalic artery and the aortic valve. A target zone can be defined as a zone including the longitudinal mid-point of the portion of the aorta extending between the brachiocephalic artery and the aortic valve, the target zone having a length of no more than about one-quarter the distance between the brachiocephalic artery and the aortic valve. A target zone can be defined as a zone including the longitudinal mid-point of the portion of the aorta extending between the brachiocephalic artery and the aortic valve, the target zone having a length of no more than about 15% of the distance between the brachiocephalic artery and the aortic valve. A target zone can be defined as a zone including the longitudinal mid-point of the portion of the aorta extending between the brachiocephalic artery and the aortic valve, the target zone having a length of no more than about 10% of the distance between the brachiocephalic artery and the aortic valve.

The superior contact position of the catheter assembly 100 can be maintained by securing a proximal portion of the catheter assembly 100 either inside or outside the vasculature or patient to continue to urge the catheter body into contact with the superior wall of the aorta at least in a part of the aortic arch.

2. Positioning Using an Inflatable Balloon Brace

Although the method of creating contact between the catheter body and a superior aspect of the aorta in at least a part of the aortic arch to maintaining a generally straight distal portion of the catheter assembly 100 is effective, another approach is to provide a positive anchor within the vasculature that can be deployed selectively as discussed above in connection with the catheter assembly 500.

Figure 15A:
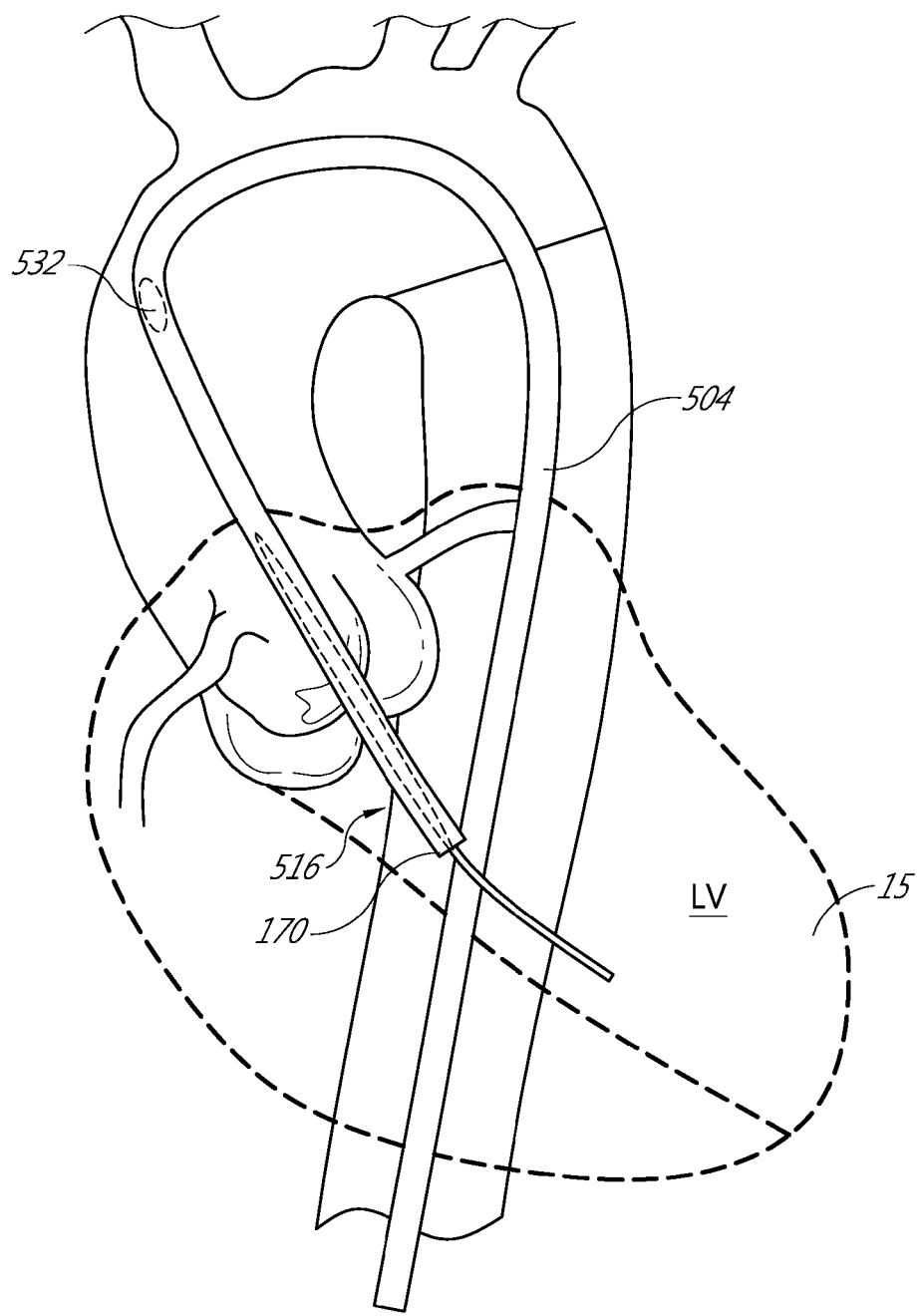
FIGS. 15A-15C are sequential views of insertion of the heart pump through the vasculature to a desired target position.
Figure 15B:
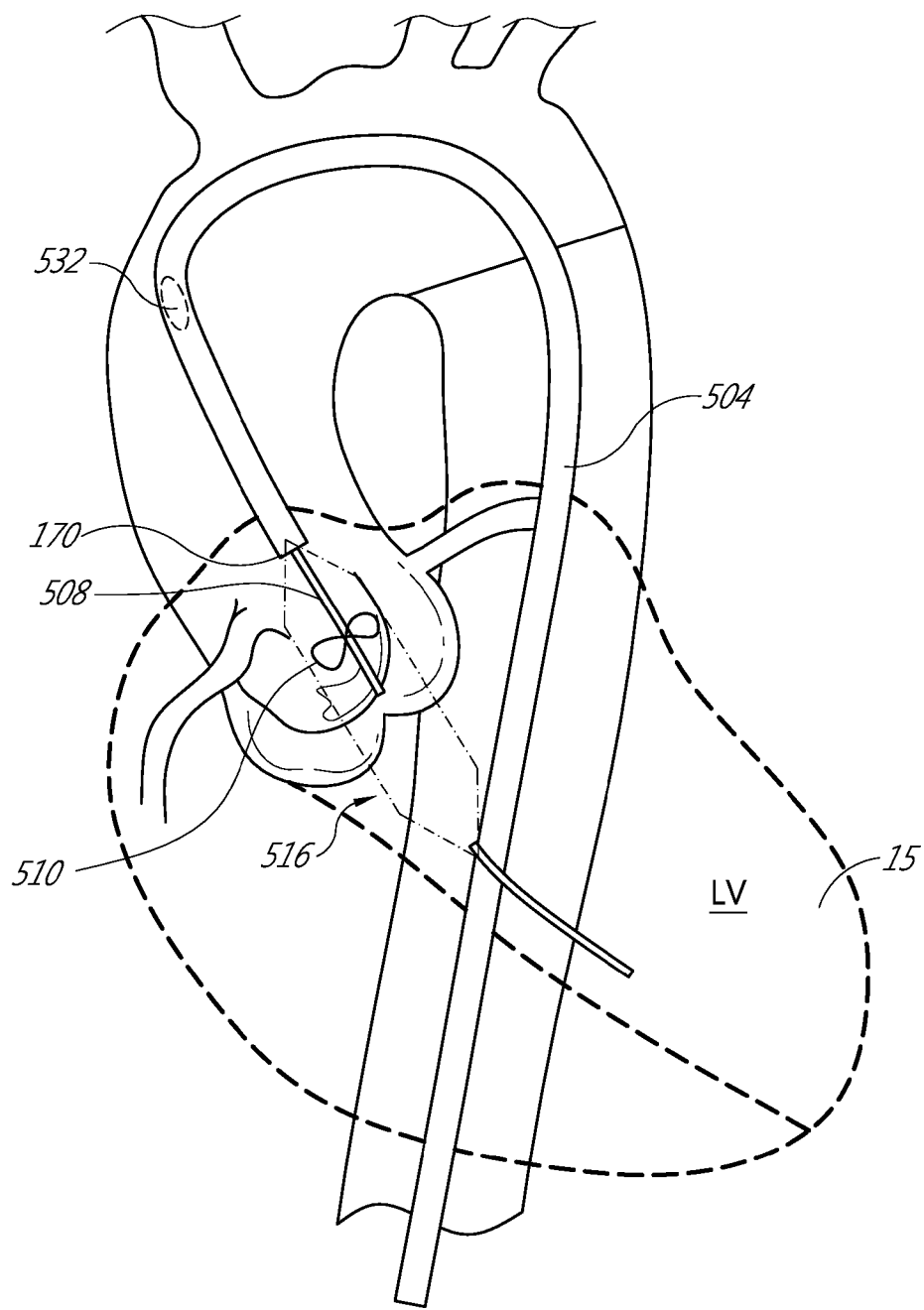
Figure 15C:
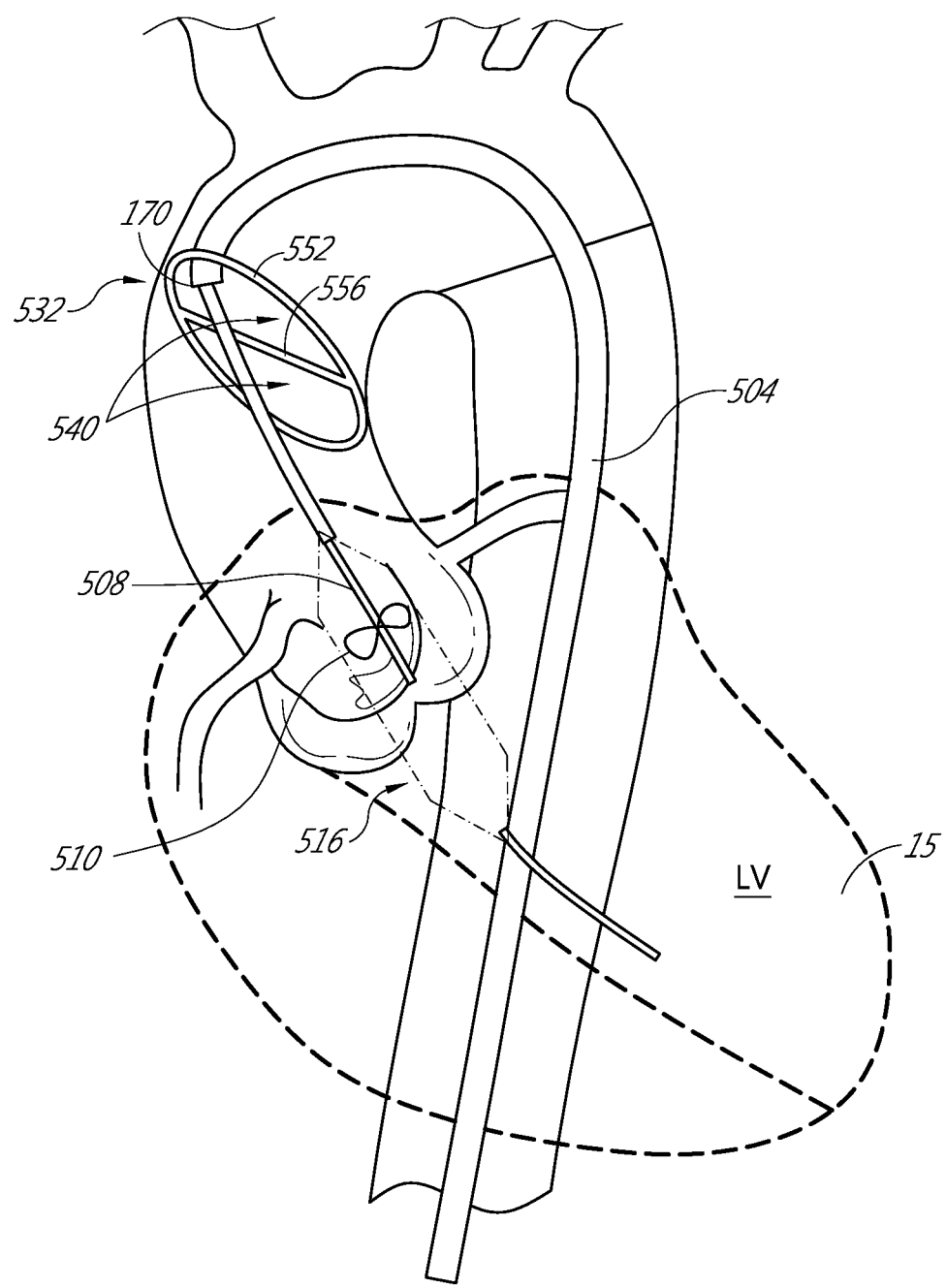

As noted above, the catheter assembly 500 can be positioned in the artery along the same trajectory as shown in FIG. 15A. Once the impeller assembly is disposed in the left ventricle LV, a distal end 170 of a sheath is withdrawn to a position proximal of the impeller 510 allowing the impeller and the cannula within which it is disposed to expand. The impeller and cannula are shown schematically in dashed lines in FIGS. 15B-15C. The balloon brace 532 can be expanded against the inside wall of the aorta. In one embodiment, the balloon brace 532 is disposed proximally of the impeller 510. The balloon brace 532 can be exposed by further withdrawing the distal end 170 to a position proximal of the balloon brace. This step is performed after the step illustrated in FIG. 15B. Thereafter, the balloon brace 532 can be expanded. In one technique the balloon brace 532 is expanded just upstream of the brachiocephalic artery. The location can be closer to the brachiocephalic artery than to the coronary arteries. The location can be upstream of but within about 2 cm of the brachiocephalic artery. The location can be upstream of but within about 4 cm of the brachiocephalic artery. When so expanded the balloon brace 532 holds the catheter assembly 500 anchored at the location upstream of the brachiocephalic artery. The trajectory upstream of the point of anchoring of the balloon brace 532 is substantially straight. The straight trajectory minimizes or reduces bending of the impeller 510 so that tip gap variation between the impeller and the inner wall of the cannula in which it is disposed is reduced or minimized. Also, the anchoring of the portion of the elongate body 504 distal of the balloon brace 532 reduces the chance of the intake of the catheter assembly 500 being expelled from the heart.

When expanded, the balloon brace 532 preserves blood flow by providing the flow-through passages 540. This ensures that flow is maintained from a distal portion of the brace 532 located at an upstream segment of the aorta extending from the heart to a downstream segment of the aorta located downstream of a proximal portion of the brace 532.

Figure 16:
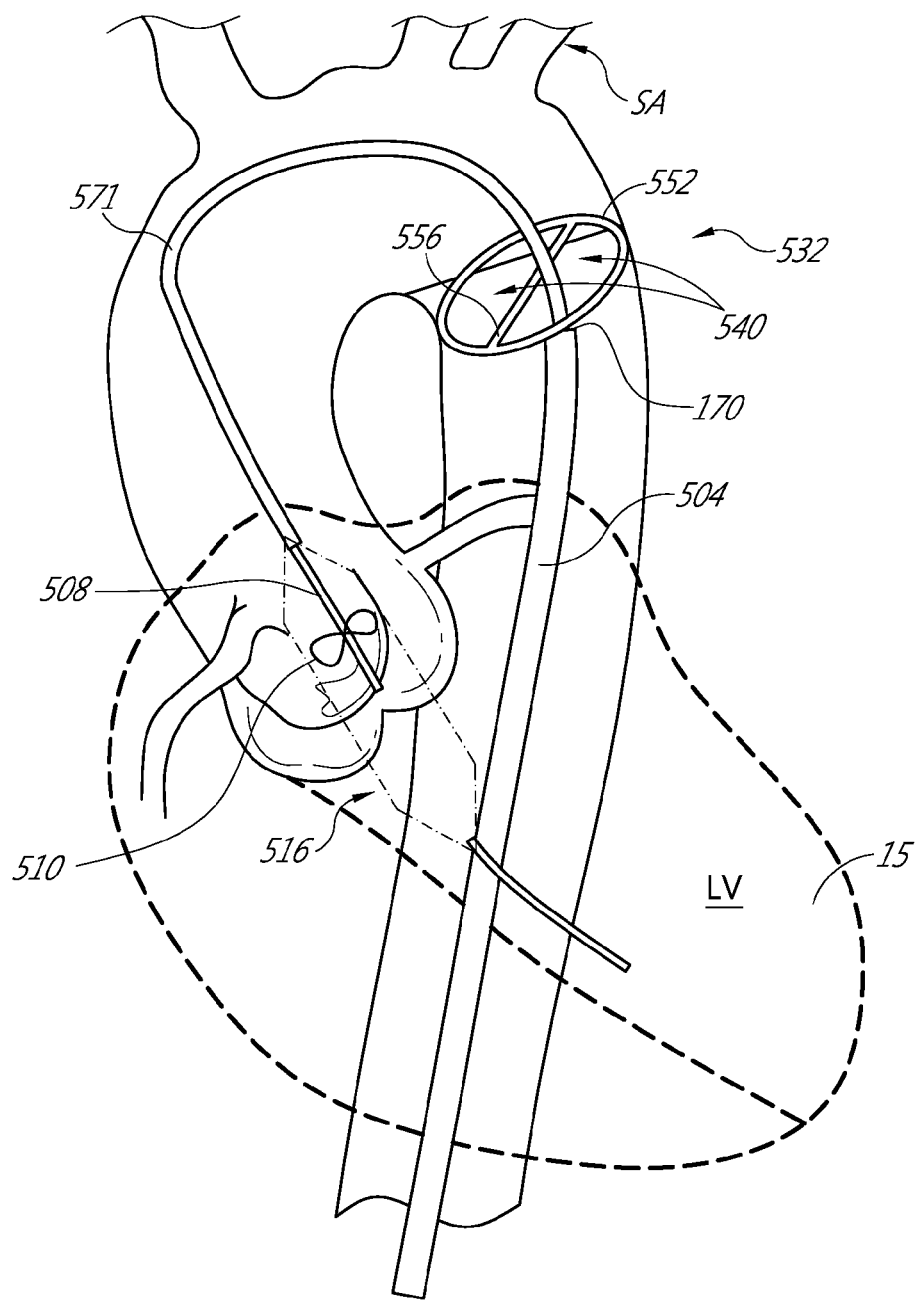
FIG. 16 shows another position for potential placement of a balloon brace.

FIG. 16 shows another method in which the balloon brace 532 is deployed in the descending aorta. In this method, the catheter assembly 500 is advanced percutaneously to the heart. The sheath 162 is retracted to expose the impeller and the cannula in which the impeller is disposed to permit the cannula and impeller to expand. The sheath 162 is further withdrawn to expose the balloon brace 532 which in this case is disposed proximally of the impeller by an amount sufficient to align the balloon brace with a segment of the aorta downstream of the subclavian artery SA. This position is advantageous in that the carotid artery and other critical arterial branches extending to the brain and arms are safely avoided. This position of the balloon brace 532 still provides a benefit in that portion of the catheter assembly 500 distal thereof is relatively short. So the movement of that portion can be more easily controlled from this location than from a more proximal location, e.g., outside the patient. The curved segment through the aortic arch can be controlled by configuring the balloon brace 532 to hold the catheter body 504 brace adjacent to and/or in contact with the superior wall of the arch. Such contact can be just distal to the balloon brace 532. The catheter body 504 can be configured (e.g., reinforced or shaped) to follow the curvature of the average arch. This configuration tends to place a distal portion 571 of the curved segment of the catheter body 504 disposed through the arch in contact with the superior aspect of the arch just upstream of the brachiocephalic artery to allow a segment distal the distal portion 571 to extend substantially straight from that location to and through the aortic valve.

As described above, the balloon brace 532 can be on the sheath 162. As such, some methods involve selecting a position to brace the catheter assembly 500. In one method, the impeller and cannula housing the impeller are expanded by withdrawing the sheath 162 to a position where the distal end 170 is proximal to these components. The clinician then determines which position of the aorta is most suitable for placement of the balloon brace 532. For example, if a straight segment from the location just upstream of the brachiocephalic artery to the aortic valve is provided, and there are no issues with critical branches or occlusions in that vascular region, the sheath 162 can be positioned to leave a distal segment thereof including the balloon brace 532 within the ascending aorta and the balloon brace is expanded in the position shown in FIG. 15C. In other variations if the clinician determines that the ascending aorta is not a good location for the balloon brace 532, the sheath 162 can be withdrawn to a position in which a distal segment thereof is in adjacent to the descending aorta. For example, a distal segment of the sheath 162 including the balloon brace 532 can be positioned just downstream from the subclavian artery SA, e.g., in a position corresponding to that of FIG. 16.

In another apparatus and method, each of the catheter body 560 and the sheath 162 includes a balloon brace 532. Where a plurality of braces are provided the catheter assembly 500 can be more securely braced, e.g., braced upstream of the brachiocephalic artery and downstream of the subclavian artery. Alternatively, the clinician can be given the option of choosing between these two positions and bracing from these two structures. In certain embodiments, the balloon brace or braces 532 can be inflated and deflated at select times and/or sequentially. In various embodiments, two or more braces or anchors are provided. In one embodiment, a brace is provided at an upstream end of the impeller and another brace is provided downstream of the impeller. This arrangement provides further support across the operative zone of the impeller. In one embodiment, two braces are provided adjacent the impeller, with one being upstream and another downstream. The braces can be attached to or integrated with the cannula housing 518. The braces can be positioned just proximal to and distal of the ends of the cannula housing. In this manner the cannula and impeller can be effectively braced during operation to reduce the risk of dislocation and undesirable vibrations.

Using balloons and other inflatable structures for the balloon brace 532 is advantageous in that the brace 532 can be easily deployed and un-deployed. This allows the clinician to easily place the balloon brace 532 and then deflate and reposition the brace. Mechanical brace members may be more difficult to retract and reposition.

Once the impeller and the balloon brace 532 are deployed, the clinician can conduct the procedure, e.g., by running the heart pump within a heart chamber. Once the procedure is finished, the clinician can remove the catheter assembly from the patient by disengaging the balloon brace 532 from the aorta (e.g., by deflating it, retracting the mechanical brace members, or capturing the brace) and by retracting the impeller.

B. Controlling the Collapse and Deployment of the Impeller Housing with the Sheath Assembly As mentioned above in Section IV(A), it can be advantageous in certain embodiments to enable a clinician to deploy and retract the impeller assembly prior to and after a heart procedure. One method of collapsing the impeller housing can be performed by advancing the sheath assembly 162 distally over the balloon brace 532 and the impeller housing to collapse the impeller assembly, e.g., for removal of the catheter assembly from the patient after a heart procedure. As mentioned above, elongate body 174 of the catheter assembly 162 can be slidably disposed over the catheter body 120. The clinician can distally advance the elongate body 174 over the impeller housing, or alternatively proximally retract the catheter body 120 such that the impeller housing collapses into the elongate body 174 of the sheath assembly 162.

As FIGS. 17A-D illustrate, the sheath assembly can have expandable distal ends 170a, 170b, 170c, that expand when a radial force is applied. Thus, when the clinician advances the elongate body 174 of the sheath over the balloon brace 532 and the impeller housing, the balloon race and the impeller housing can contact the distal end 170 and can induce a radial force that causes the distal ends 170a, 170b, 170c, to expand in order to aid in retraction of the impeller assembly. Similarly, when the clinician slides the elongate body 174 in a proximal direction, the impeller assembly can deploy through the distal end 170 of the catheter assembly 162, because the distal ends 170a, 170b, 170c, can contract when a radial force is removed (or not applied). Thus, the clinician can reliably deploy and retract the impeller assembly by sliding the elongate body 174 of the sheath relative to the catheter body 120. In other embodiments, the sheath assembly need not have expandable distal ends as described above. The clinician can therefore simply deploy the impeller assembly 116 by providing relative motion between the elongate body 174 of the sheath and the balloon brace and impeller assembly, e.g., by retracting the elongate body 174 from the impeller assembly, and can collapse the impeller assembly by providing relative motion between the elongate body 174 of the sheath and the impeller assembly 116, e.g., by advancing the elongate body over the impeller assembly. The distal end of the elongate body 174 can therefore effectuate collapse of the balloon brace 532 and the impeller assembly 116 without using the expandable distal ends described above. In embodiments where the impeller assembly is self-expanding, the retraction of the elongate body 174 from the impeller assembly 116 or extension of the impeller assembly 116 out of the elongate body 174 can release the impeller assembly to self-expand.

Although the inventions herein have been described with reference to particular embodiments, it is to be understood that these embodiments are merely illustrative of the principles and applications of the present inventions. It is therefore to be understood that numerous modifications can be made to the illustrative embodiments and that other arrangements can be devised without departing from the spirit and scope of the present inventions as defined by the appended claims. Thus, it is intended that the present application cover the modifications and variations of these embodiments and their equivalents.

What is claimed is:

1. A catheter pump assembly, comprising:
   an elongate body assembly having a proximal end, a distal end and at least one lumen extending therebetween;
   a shaft disposed at least partially within the elongate body and journaled for rotation;
   an impeller coupled with a distal portion of the shaft, the impeller configured to be rotated to induce flow of blood when the impeller is placed in fluid communication with a source of blood; and
   an anchor disposed along an outer surface of the catheter pump assembly at an intermediate location and configured to be deployed therefrom to engage a vascular segment to hold in place a portion of the catheter pump assembly disposed in the patient.

2. The catheter pump assembly of claim 1, wherein the anchor comprises an inflatable balloon brace disposed on an outer surface of the catheter pump assembly, the inflatable balloon brace being spaced proximally from the impeller and having a low profile configuration for delivery through the vasculature and an expanded configuration for disposing the impeller within the source of blood.

3. The catheter pump assembly of claim 2, wherein the inflatable balloon brace comprises the at least one flow-through channel disposed therein.

4. The catheter pump assembly of claim 3, wherein the at least one channel is bounded by the inflatable balloon brace or by the elongate body.

5. The catheter pump assembly of claim 2, wherein the elongate body assembly comprises a catheter body and a sheath disposed over the catheter body, the inflatable balloon brace being disposed on the catheter body.

6. The catheter pump assembly of claim 5, wherein the sheath comprises a cylindrical distal portion surrounding the catheter body, the sheath comprising a first position in which the cylindrical distal portion is disposed over the inflatable balloon brace and a second position which the inflatable balloon brace is exposed.

7. The catheter pump assembly of claim 1, wherein the elongate body assembly has a length sufficient to extend from a peripheral vascular location to a ventricle of the heart.

8. The catheter pump assembly of claim 2, wherein the inflatable brace is positioned on the elongate body assembly such that when the elongate body assembly extends between the left ventricle and a peripheral arterial location, the inflatable brace is disposed in the descending aorta.

9. The catheter pump assembly of claim 2, wherein the inflatable brace is configured to bias a portion of the elongate body assembly against a superior aspect of the aortic arch when the elongate body assembly extends between the left ventricle and a peripheral vascular location.

10. The catheter pump assembly of claim 2, wherein the inflatable brace comprises a torus portion, wherein the elongate body assembly is disposed between the torus and the axis of revolution of the torus portion.

11. The catheter pump assembly of claim 10, wherein the torus portion is disposed about a portion of the elongate body assembly and further comprises an inflation channel extending between an inflation lumen in the elongate body assembly and an interior space of the torus.

12. The catheter pump assembly of claim 11, further comprising one or more blood flow channels defined at least in part by a surface of the torus.

13. The catheter pump assembly of claim 1, wherein the anchor comprises a plurality of lobes having a compressed configuration and an expanded configuration, the lobes extending outwardly from the elongate body assembly in the expanded configuration such that distal ends of the lobes contact the vascular segment during operation of the catheter pump assembly.

14. A method of positioning a catheter pump, comprising:
inserting a catheter pump into a peripheral vascular location, the catheter pump having an elongate body, a flow generating device disposed at a distal portion of the elongate body, and an anchor disposed proximally of the flow generating device;
advancing the distal portion of the elongate body to a source of blood;
expanding the brace from a side surface of the elongate body into contact with a target location within the patient; and
operating the flow generating device within the source of blood to induce a blood flow.

15. The method of claim 14, wherein the brace comprises an inflation chamber in fluid communication with an inflation lumen disposed in the elongate body and wherein expanding the brace comprises flowing an inflation medium into the inflation chamber.

16. The method of claim 14, wherein advancing comprises positioning the flow generating device in fluid communication with a left ventricle.

17. The method of claim 16, wherein advancing comprises positioning the flow generating device at least partially within the left ventricle.

18. The method of claim 14, wherein the target location includes the descending aorta between the left subclavian artery and the peripheral vascular location.

19. The method of claim 14, wherein the target location includes the ascending aorta between the heart and the brachiocephalic artery.

20. The method of claim 14, wherein the target location includes the ascending aorta between the coronary arteries and brachiocephalic artery.

21. The method of claim 14, wherein the brace is configured to position the distal portion asymmetrically in the vasculature when inflated, and further comprising orienting the elongate body such that the distal portion of the elongate body extends between a central region of and an outer wall of the ascending aorta.

* * * * *